(12) United States Patent
Maness

(10) Patent No.: US 8,616,397 B2
(45) Date of Patent: Dec. 31, 2013

(54) PHARMACEUTICAL WASTE DISPOSAL ASSEMBLY INCLUDING WASTE DIVERTER

(75) Inventor: David A. Maness, Mt. Pleasant, SC (US)

(73) Assignee: Cactus, LLC, Charleston, SC (US)

( * ) Notice: Subject to any disclaimer, the term of this patent is extended or adjusted under 35 U.S.C. 154(b) by 474 days.

(21) Appl. No.: 13/097,351

(22) Filed: Apr. 29, 2011

(65) Prior Publication Data

US 2011/0259467 A1 Oct. 27, 2011

Related U.S. Application Data

(63) Continuation-in-part of application No. 12/768,044, filed on Apr. 27, 2010.

(51) Int. Cl.
  *B65D 81/26* (2006.01)
(52) U.S. Cl.
  USPC .... 220/4.12; 220/23.88; 220/553; 220/908.3; 206/204; 206/366; 206/370
(58) Field of Classification Search
  USPC .......... 141/331, 340–341; 206/204, 363–366, 206/370; 220/4.12, 23.87–23.89, 553, 220/908.3
  See application file for complete search history.

(56) References Cited

U.S. PATENT DOCUMENTS

| | | | |
|---|---|---|---|
| 3,643,266 A | 2/1972 | Black | |
| 4,050,894 A * | 9/1977 | Genis | 206/363 |
| 4,801,034 A | 1/1989 | Sandomeno | |
| 4,816,307 A | 3/1989 | Honeycutt | |
| 5,022,548 A | 6/1991 | Stakis | |
| 5,038,929 A | 8/1991 | Kubofcik | |
| 5,097,950 A * | 3/1992 | Weiss et al. | 206/366 |
| 5,111,958 A | 5/1992 | Witthoeft | |
| 5,167,193 A | 12/1992 | Withers et al. | |
| 5,245,117 A | 9/1993 | Withers et al. | |
| 5,273,161 A | 12/1993 | Sagstetter | |
| 5,323,719 A | 6/1994 | Withers et al. | |
| 5,372,252 A * | 12/1994 | Alexander | 206/210 |
| 5,385,105 A | 1/1995 | Withers et al. | |
| 5,411,193 A * | 5/1995 | Culp | 224/669 |
| 5,458,072 A | 10/1995 | Hughes et al. | |
| 5,483,999 A | 1/1996 | Lampropoulos et al. | |

(Continued)

FOREIGN PATENT DOCUMENTS

WO  WO2009141583  11/2009

*Primary Examiner* — Gregory Huson
*Assistant Examiner* — Nicolas A Arnett
(74) *Attorney, Agent, or Firm* — Roeder & Broder LLP; James P. Broder

(57) ABSTRACT

A pharmaceutical waste disposal assembly (10) for disposing of one or more of fluid pharmaceutical waste and solid pharmaceutical waste includes a first waste receiver (614) and a receiver retainer (16). The first waste receiver (614) includes a first receiver body (621) having a first body access (621BA). Additionally, the pharmaceutical waste moves in a first direction (695C) toward the first body access (621BA) through which the pharmaceutical waste is directly received by the first receiver body (621). The receiver retainer (16) substantially encloses the first waste receiver (614). Further, the first waste receiver (614) is removable from the receiver retainer (16). Moreover, one of the first waste receiver (614) and the receiver retainer (16) includes a first waste guide (667A) that guides the pharmaceutical waste in a second direction (695A) away from the first body access (621BA) and in the first direction (695C) toward the first body access (621BA). Additionally, the first waste guide (667A) inhibits removal of the pharmaceutical waste from the first receiver body (621).

25 Claims, 20 Drawing Sheets

(56) References Cited

U.S. PATENT DOCUMENTS

| | | | |
|---|---|---|---|
| 5,495,941 A | 3/1996 | Leonard | |
| 5,595,711 A | 1/1997 | Wilson et al. | |
| 5,641,947 A | 6/1997 | Riddle, Jr. | |
| 5,707,173 A | 1/1998 | Cottone et al. | |
| 5,735,834 A | 4/1998 | Hemstreet et al. | |
| 5,792,126 A | 8/1998 | Tribastone et al. | |
| 5,947,285 A | 9/1999 | Gaba et al. | |
| 6,010,444 A | 1/2000 | Honeycutt et al. | |
| 6,053,314 A | 4/2000 | Pittman | |
| 6,090,572 A | 7/2000 | Crosby | |
| 6,247,592 B1 * | 6/2001 | Racicot et al. | 206/366 |
| 6,719,017 B1 * | 4/2004 | McArthur et al. | 141/86 |
| 6,733,481 B2 | 5/2004 | Ow | |
| 6,797,857 B2 | 9/2004 | Tanhehco | |
| 7,119,689 B2 | 10/2006 | Mallett et al. | |
| 7,123,150 B2 | 10/2006 | Mallett et al. | |
| 7,126,480 B2 | 10/2006 | Mallett et al. | |
| 7,138,918 B2 | 11/2006 | Mallett et al. | |
| 7,258,711 B2 | 8/2007 | Dunn et al. | |
| 7,275,645 B2 | 10/2007 | Mallett et al. | |
| 7,296,688 B2 | 11/2007 | Mallett et al. | |
| 7,303,080 B2 | 12/2007 | Mallett et al. | |
| 7,303,081 B2 | 12/2007 | Mallett et al. | |
| 7,303,082 B2 | 12/2007 | Mallett et al. | |
| 7,311,207 B2 | 12/2007 | Mallett et al. | |
| 7,341,147 B2 | 3/2008 | Mallett et al. | |
| 7,383,195 B2 | 6/2008 | Mallett et al. | |
| 7,454,358 B2 | 11/2008 | Mallett et al. | |
| 7,483,837 B2 | 1/2009 | Mallett et al. | |
| 7,487,100 B2 | 2/2009 | Mallett et al. | |
| 7,490,722 B2 | 2/2009 | Mayda et al. | |
| 7,533,028 B2 | 5/2009 | Mallett et al. | |
| 7,533,029 B2 | 5/2009 | Mallett et al. | |
| 7,562,025 B2 | 7/2009 | Mallett et al. | |
| 7,565,299 B2 | 7/2009 | Mallett et al. | |
| 7,600,638 B2 | 10/2009 | Finnestad et al. | |
| 7,617,113 B2 | 11/2009 | Mallett et al. | |
| 7,620,559 B2 | 11/2009 | Mallett et al. | |
| 7,660,724 B2 | 2/2010 | Mallett et al. | |
| 7,665,491 B2 * | 2/2010 | Lampropoulos | 141/311 A |
| 7,918,777 B2 * | 4/2011 | Parrott | 588/249.5 |
| 8,348,056 B2 * | 1/2013 | Maness | 206/366 |
| 8,393,488 B2 * | 3/2013 | Japuntich et al. | 220/254.1 |
| 8,534,459 B2 * | 9/2013 | Maness | 206/366 |
| 2002/0095125 A1 | 7/2002 | Parker | |
| 2002/0100706 A1 * | 8/2002 | Sherman et al. | 206/370 |
| 2003/0164600 A1 | 9/2003 | Dunn et al. | |
| 2004/0144682 A1 | 7/2004 | Altmayer | |
| 2004/0236292 A1 | 11/2004 | Tazoe et al. | |
| 2005/0103662 A1 | 5/2005 | Iske et al. | |
| 2005/0106087 A1 | 5/2005 | Tanhehco | |
| 2005/0267425 A1 | 12/2005 | Castora et al. | |
| 2006/0212306 A1 | 9/2006 | Mallett et al. | |
| 2007/0160789 A1 * | 7/2007 | Merical et al. | 428/35.7 |
| 2007/0224077 A1 | 9/2007 | Cox et al. | |
| 2007/0267304 A1 * | 11/2007 | Portier | 206/204 |
| 2008/0058736 A1 | 3/2008 | Reshamwala | |
| 2010/0076244 A1 | 3/2010 | Parrott | |
| 2011/0259471 A1 * | 10/2011 | Maness | 141/69 |
| 2011/0297567 A1 * | 12/2011 | Maness | 206/366 |
| 2012/0006697 A1 * | 1/2012 | Portier et al. | 206/204 |
| 2012/0168443 A1 * | 7/2012 | Maness | 220/315 |
| 2012/0305132 A1 * | 12/2012 | Maness | 141/69 |

* cited by examiner

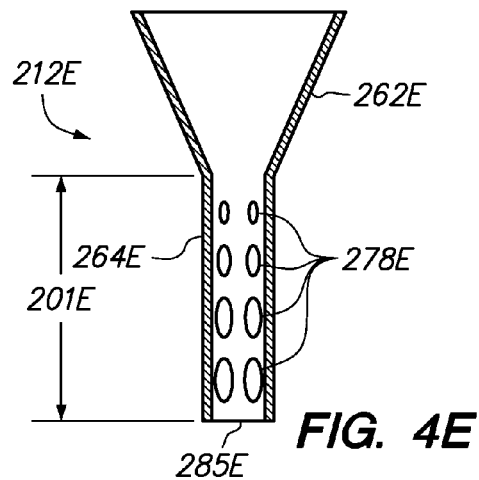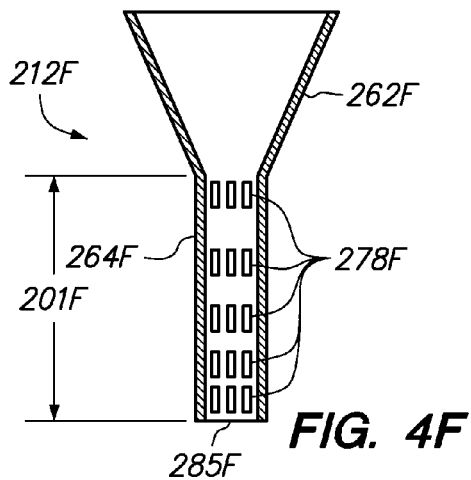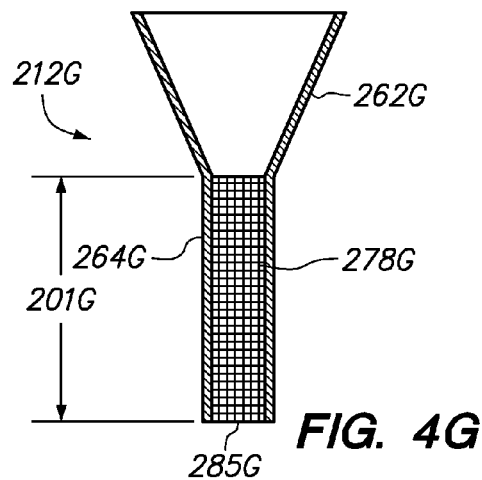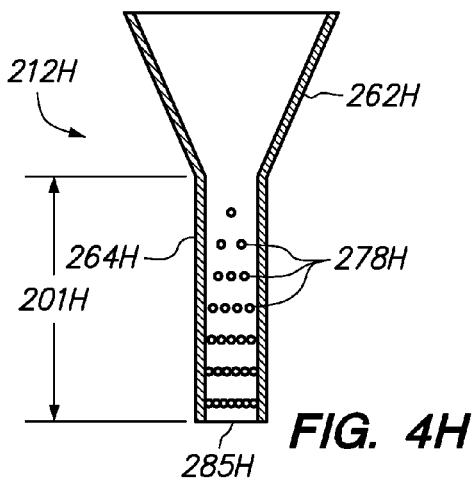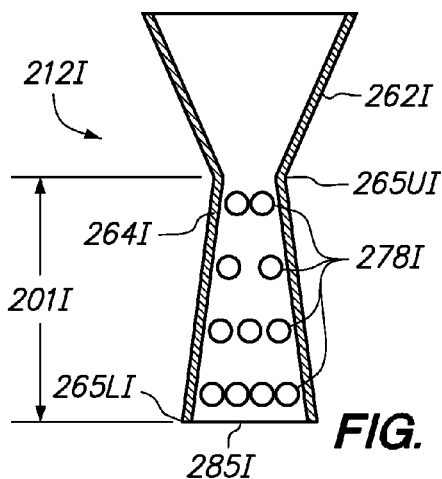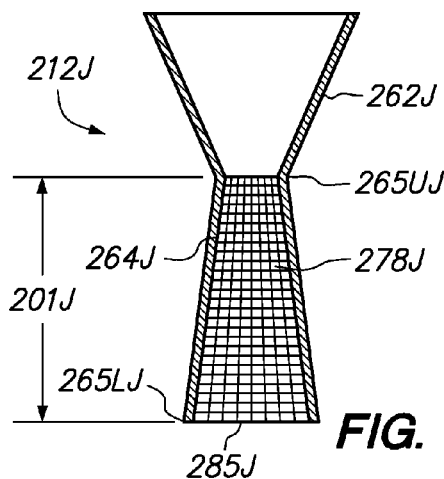

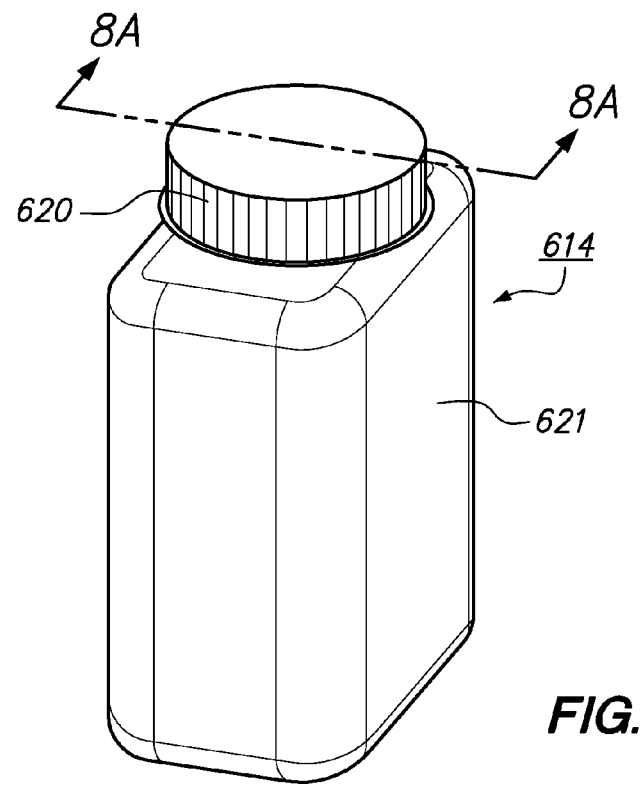
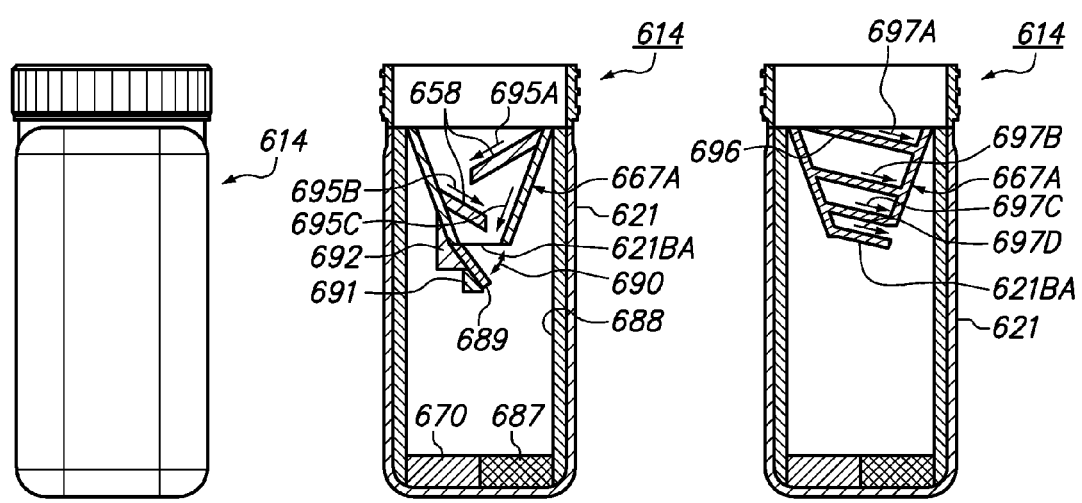
FIG. 6
FIG. 7   FIG. 8A   FIG. 8B

PHARMACEUTICAL WASTE DISPOSAL ASSEMBLY INCLUDING WASTE DIVERTER

RELATED APPLICATION

The present application is a continuation-in-part application and claims the benefit under 35 U.S.C. 120 on co-pending U.S. patent application Ser. No. 12/768,044, filed on Apr. 27, 2010. To the extent permitted, the contents of U.S. patent application Ser. No. 12/768,044 are incorporated herein by reference.

BACKGROUND

The disposal of pharmaceutical waste has long been a concern of those in the medical care industry. Pharmaceutical waste can include both liquids and solids, such as expired medicines, partially filled vials, compounded IV's, broken or spilled materials, undispensed compounded products, discontinued indated items, unused unit dosed items, unused IV's, patients' personal medications, and certain hazardous waste materials, to name a few. Further, pharmaceutical waste can be "raw", such that the waste does not include any sort of container or packaging, or the waste can be contained in a container such as a bottle, vial, bag, dispenser, syringe, or any other type of packaging. By way of example and not of limitation, raw waste can include various liquids such as the fluid from a syringe, bag or bottle, or solids such as pills, capsules, powders, patches, etc. Ensuring that such waste does not wind up in the hands of unauthorized personnel, migrate to our waterways or bodies of water, or that illegal diversion does not occur, has been of primary importance not only in the pharmaceutical/medical industry, but in the environmental field as well. Currently, the Resource Conservation Recovery Act (RCRA) provides strict mandates for waste disposal and/or management. In fact, failure to comply with these RCRA regulations can result in the imposition of sizable monetary fines.

Hazardous waste, which includes chemicals or formulations deemed to be so detrimental to the environment that they must be segregated for special waste management, cannot legally be sewered or landfilled. Importantly, a number of relatively common drug entities and pharmaceutical formulations meet the definition of hazardous waste. As non-exclusive examples, drugs such as epinephrine, nitroglycerin, warfarin, nicotine and various chemotherapy agents fall into this hazardous waste category. The Environmental Protection Agency (EPA) defines characteristics of hazardous waste, including ignitability, toxicity, corrosivity and reactivity. Under conventional disposal methods, the acceptable means by which pharmaceutical waste may be disposed and treated are dependent upon the specific type of waste.

Historically, pharmaceutical waste has been disposed of by a variety of means including disposal in waste receptacles, sharps containers, sewering or incineration, to name a few. However, hospital incinerators are becoming much less preferred, and shipment of the waste to outside waste disposal firms may be required. Unfortunately, a substantial amount of solid or liquid pharmaceutical waste in a hospital setting is wrongfully deposited into biohazardous sharps containers, which are designed for receiving used/contaminated syringes and/or hypodermic needles. Alternatively, pharmaceutical waste is simply thrown in the trash or dumped down a drain, rather than utilizing a dedicated pharmaceutical waste system.

Attempts to address these issues have not been altogether satisfactory. For example, some relatively expensive waste receiver systems require that the waste drug remain in its original bar-coded container, which may be impractical in certain situations, such as raw waste. Additionally, utilizing dozens or even hundreds of these types of waste disposal systems in a hospital can be cost-prohibitive. Further, the size of these types of waste disposal systems may make providing such a system at each point of use around a health care facility unfeasible. Moreover, such systems can be relatively heavy and difficult to move, and can take up a substantial amount of valuable floor space in a hospital, for example.

SUMMARY

The present invention is directed toward a pharmaceutical waste disposal assembly for disposing of one or more of fluid pharmaceutical waste and solid pharmaceutical waste. In various embodiments, the pharmaceutical waste disposal assembly includes a first waste receiver and a receiver retainer. The first waste receiver includes a first receiver body having a first body access. Additionally, the pharmaceutical waste moves in a first direction toward the first body access through which the pharmaceutical waste is directly received by the first receiver body. The receiver retainer substantially encloses the first waste receiver. Further, the first waste receiver is removable from the receiver retainer. Moreover, one of the first waste receiver and the receiver retainer includes a first waste guide that guides the pharmaceutical waste in a second direction away from the first body access and in the first direction toward the first body access.

In one embodiment, the first waste guide includes a spiral funnel that guides the pharmaceutical waste in the second direction away from the first body access prior to guiding the pharmaceutical waste in the first direction toward the first body access. Alternatively, in one embodiment, the first waste guide includes a series of diverters that guides the pharmaceutical waste in the second direction away from the first body access prior to guiding the pharmaceutical waste in the first direction toward the first body access.

Additionally, in certain embodiments, the first waste guide can guide the pharmaceutical waste in a third direction away from the first body access prior to guiding the pharmaceutical waste in the first direction toward the first body access. The third direction is different than the second direction. Further, in one such embodiment, the first waste guide can guide the pharmaceutical waste in a fourth direction away from the first body access prior to guiding the pharmaceutical waste in the first direction toward the first body access. The fourth direction is different than the second direction and the third direction.

In one embodiment, the first waste receiver is a solid waste receiver including a solid receiver body that receives the solid pharmaceutical waste. Alternatively, in one embodiment, the first waste receiver is a fluid waste receiver including a fluid receiver body that receives the fluid pharmaceutical waste.

Further, in one embodiment, the pharmaceutical waste disposal assembly can further comprise a second waste guide that guides the pharmaceutical waste in a third direction away from the first body access and a fourth direction toward the first body access. In such embodiment, the first waste receiver includes the first waste guide and the receiver retainer includes the second waste guide.

Additionally, in some embodiments, the pharmaceutical waste disposal assembly can further comprise a second waste receiver including a second receiver body having a second body access. In such embodiments, the pharmaceutical waste moves in a third direction toward the second body access through which the pharmaceutical waste is directly received by the second receiver body. Further, the receiver retainer substantially encloses the second waste receiver. Moreover, one of the second waste receiver and the receiver retainer includes a second waste guide that guides the pharmaceutical waste in a fourth direction away from the second body access and in the third direction toward the second body access.

Further, in one embodiment, the first waste receiver is a solid waste receiver including a solid receiver body that receives the solid pharmaceutical waste. In such embodiment, the second waste receiver is a fluid waste receiver including a fluid receiver body that receives the fluid pharmaceutical waste. Moreover, the second waste receiver can be removable from the receiver retainer.

Still further, in one embodiment, the first waste guide includes a guide flap near the first body access. The guide flap moves between an open position and a closed position. In such embodiment, when the first waste receiver is moved to an inverted position, the guide flap moves to the closed position so that the pharmaceutical waste is inhibited from exiting the first receiver body.

Additionally, in some embodiments, the first waste guide inhibits removal of the pharmaceutical waste from the first receiver body.

Yet further, the present invention is directed toward a method for disposing of one or more of fluid pharmaceutical waste and solid pharmaceutical waste.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIGS. 4E-4J are various cross-sectional views of non-exclusive alternative embodiments of a portion of the fluid waste receiver;

FIG. 6 is a perspective view of one embodiment of the solid waste receiver having features of the present invention;

FIG. 7 is a front elevation of the solid waste receiver illustrated in FIG. 6;

FIG. 8A is a cross-sectional view of a portion of the solid waste receiver taken on line 8-8 in FIG. 6;

FIG. 8B is an alternative cross-sectional view of a portion of the solid waste receiver taken on line 8-8 in FIG. 6;

DESCRIPTION

Figure 1A:
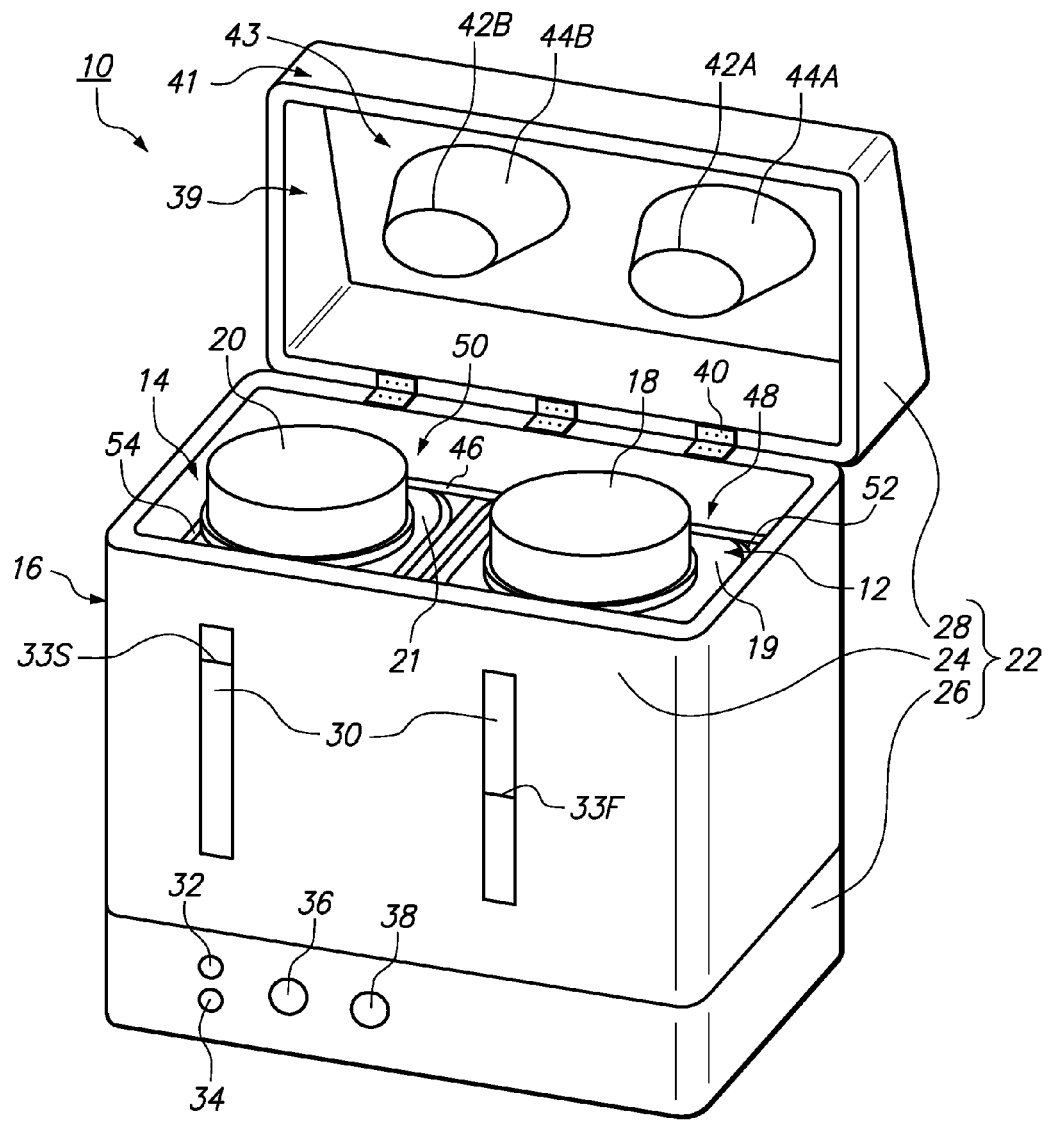
FIG. 1A is a perspective view of one embodiment of a pharmaceutical waste disposal assembly having features of the present invention, illustrated in an open position, including a fluid waste receiver, a solid waste receiver and a receiver retainer.

FIG. 1A is a perspective view of one embodiment of a pharmaceutical waste disposal assembly 10 (also sometimes referred to herein as a "disposal assembly"), shown in an open position. In one embodiment, the disposal assembly 10 provides a means for disposing of fluid and/or solid pharmaceutical and/or medical waste (generically referred to herein as "waste") which can ultimately be incinerated or otherwise treated and/or permanently disposed of. The design of the disposal assembly 10 can vary depending upon the specific application and/or location of the disposal assembly 10. In the embodiment illustrated in FIG. 1A, the disposal assembly 10 includes a fluid waste receiver 12, a solid waste receiver 14 and a receiver retainer 16.

In this embodiment, the fluid waste receiver 12 can receive waste in a liquid and/or a gaseous phase of matter. The design of the fluid waste receiver 12, including the size, volume, shape and specific materials that form the fluid waste receiver 12, can vary depending upon the design requirements of the disposal assembly 10. In the embodiment illustrated in FIG.

1A, the fluid waste receiver 12 includes a fluid receiver cap 18 and a fluid receiver body 19 (also sometimes referred to herein as "receiver body"). The fluid receiver cap 18 covers a fluid receiver opening (not illustrated in FIG. 1A) which provides access into an interior of the fluid waste receiver 12. In one embodiment, the fluid receiver cap 18 can be a tamper-resistant, locking cap that is positioned on the fluid waste receiver 12 once the fluid waste receiver 12 has reached a predetermined capacity or weight of fluid waste, has been in use for a predetermined duration of time, or is otherwise determined to be no longer suitable for receiving fluid waste. For example, the fluid receiver cap 18 can include a one-way ratchet ring that interlocks with the fluid receiver body 19.

The fluid receiver body 19 is configured to receive fluid waste that is deposited into the fluid waste receiver 12. The fluid receiver body 19 can be formed from any suitably durable materials. In one embodiment, the fluid receiver body 19 can be formed from a durable injection-molded plastic material. Alternatively, the fluid receiver body 19 can be formed from fiberglass, glass, ceramic, various metals, a composite material, or a combination thereof, as non-exclusive examples. In one embodiment, the material that forms the fluid receiver body 19 can be clear or otherwise see-through to allow a user to observe the level of waste within the fluid waste receiver 12. Alternatively, the material that forms the fluid receiver body 19 can be opaque or otherwise non-see-through.

Figure 4A:
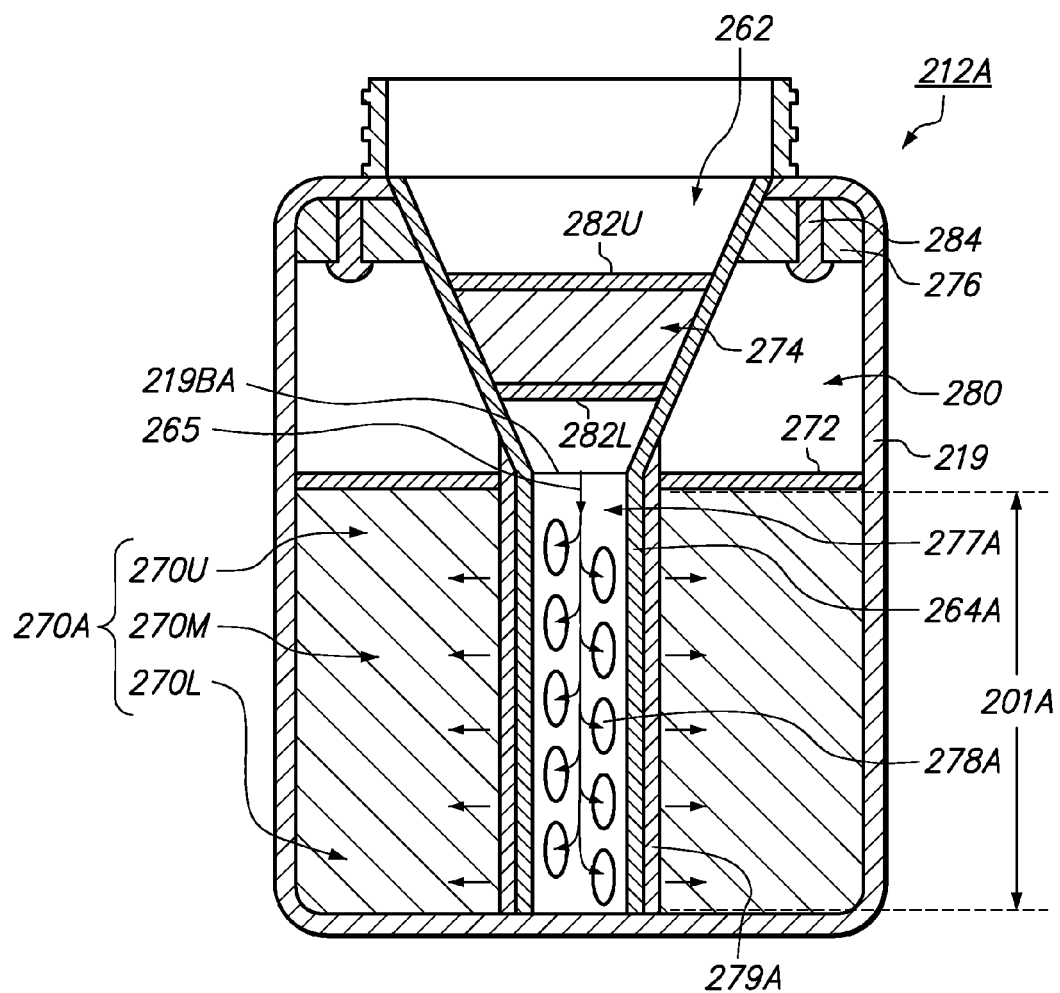
FIG. 4A is a cross-sectional view of a portion of the fluid waste receiver taken on line 4A-4A in FIG. 2.

In certain embodiments, the fluid receiver body 19 includes a fluid body access 219BA (e.g., as illustrated in FIG. 4A) through which the fluid pharmaceutical waste is directly received by the fluid receiver body 19.

In one embodiment, the fluid waste receiver 12 can have a capacity of approximately 2.0 liters. Alternatively, the fluid waste receiver 12 can have a capacity of greater than or less than 2.0 liters. It is recognized that the capacity of the fluid waste receiver 12 can be commensurate with the purpose and/or location of the disposal assembly 10. For example, the disposal assembly 10 that is used inside of a patient's room can have a fluid waste receiver 12 with a relatively small capacity. Conversely, the disposal assembly 10 that is used in a pharmacy may have a fluid waste receiver 12 with a relatively large capacity.

The solid waste receiver 14 receives waste in a solid phase of matter. The design of the solid waste receiver 14, including the size, volume, shape and specific materials that form the solid waste receiver 14, can vary depending upon the design requirements of the disposal assembly 10. In the embodiment illustrated in FIG. 1A, the solid waste receiver 14 includes a solid receiver cap 20 that can be substantially similar to the fluid receiver cap 18 previously described.

In one embodiment, the solid receiver cap 20 can be a tamper-resistant, locking cap that is positioned on the solid waste receiver 14 once the solid waste receiver 14 has reached a predetermined capacity or weight of solid waste, has been in use for a predetermined duration of time, or is otherwise determined to be no longer suitable for receiving solid waste.

In one embodiment, the solid waste receiver 14 can have a capacity of approximately 1.0 liter. Alternatively, the solid waste receiver 14 can have a capacity of greater than or less than 1.0 liter. Somewhat similar to the fluid waste receiver 12, it is recognized that the capacity of the solid waste receiver 14 can be commensurate with the purpose and/or location of the disposal assembly 10. For example, the disposal assembly 10 that is used inside of a patient's room can have a solid waste receiver 14 with a relatively small capacity. Conversely, the disposal assembly 10 that is used in a pharmacy may have a solid waste receiver 14 with a relatively large capacity.

The solid waste receiver 14 includes a solid receiver body 21 that contains the solid waste. The solid receiver body 21 can be formed from any suitably durable materials. In one embodiment, the solid receiver body 21 can be formed from a durable plastic material. Alternatively, the solid receiver body 21 can be formed from glass, ceramic, various metals, or a composite material, as non-exclusive examples. In one embodiment, the material that forms the solid receiver body 21 can be clear or otherwise see-through to allow a user to observe the level of waste within the solid waste receiver 14. Alternatively, the material that forms the solid receiver body 21 can be opaque or otherwise non-see-through.

In certain embodiments, the solid receiver body 21 includes a solid body access 621BA (e.g., as illustrated in FIG. 8A) through which the fluid pharmaceutical waste is directly received by the solid receiver body 21.

In one embodiment, the solid waste receiver 14 is a separate structure from the fluid waste receiver 12. In an alternative embodiment, the solid waste receiver 14 and the fluid waste receiver 12 can be integrated and formed as a unitary structure.

In the embodiment illustrated in FIG. 1A, the receiver retainer 16 retains the fluid waste receiver 12 and the solid waste receiver 14. In an alternative embodiment (not shown), the receiver retainer 16 can retain either the fluid waste receiver 12 or the solid waste receiver 14. In the embodiment illustrated in FIG. 1A, the receiver retainer includes a retainer housing 22 including one or more retainer side walls 24, a retainer base 26 and a retainer lid 28. In one embodiment, the retainer housing 22 includes four retainer side walls 24, although it is recognized that the retainer housing 22 can include any suitable number of retainer side walls 24. Further, although the retainer housing 22 illustrated in FIG. 1A has a rectangular configuration, it is understood that the retainer housing 22 can have another suitable configuration, such as cylindrical, triangular, pyramidal, rhomboidal or any other suitable three-dimensional polygonal configuration.

In the embodiment illustrated in FIG. 1A, one or more of the retainer side walls 24 can include one or more viewing windows 30 to allow a user to view a fluid waste level 33F and/or a solid waste level 33S in the corresponding waste receiver 12, 14. This design provides an alternative or backup means for determining whether the particular waste receiver 12, 14 needs to be removed and replaced based on the amount of waste in the waste receiver 12, 14.

In the embodiment illustrated in FIG. 1A, the retainer base 26 can include various indicator devices to inform the user of certain useful information. For example, in one embodiment, the retainer base 26 can include a charged battery indicator 32 and/or a low battery indicator 34. These indicators 32, 34 can be in the form of lights, audible indicators, digital readouts, gauges, or any other suitable type of indicator. These indicators 32, 34 automatically activate depending upon the charge status of a electrochemical cell structure 68 e.g., battery (illustrated in FIG. 1C).

The retainer base 26 may also include one or more fluid waste receiver indicators 36 (only one fluid receiver indicator 36 is illustrated in FIG. 1A) and/or one or more solid waste receiver indicators 38 (only one solid receiver indicator 38 is illustrated in FIG. 1A). The purpose for and number of the waste receiver indicators 36, 38 can vary. For example, the waste receiver indicators 36, 38 can alert the user that a predetermined capacity and/or weight of one or both of the waste receivers 12, 14 has been reached or exceeded. Alternatively, or in addition, the indicators 36, 38 can alert the user that a predetermined date and/or time has arrived, which can signal a requirement or recommendation for immediate or imminent removal and/or replacement of one or both of the waste receivers 12, 14. The indicators 36, 38 can be in the form of one or more lights, audible alerts, digital readouts, gauges, or any other suitable type of indicator for providing a user with certain useful information pertaining to one or more of the waste receivers 12, 14 and/or their contents. Additionally, although two indicators 36, 38 are illustrated in FIG. 1A, additional waste receiver indicators can be included.

As one non-exclusive example, in the event that the maximum time the fluid waste receiver 12 can be utilized is 90 days, one of the indicators 36, 38 can be activated a predetermined number of days before expiration of the 90 day period, i.e. 15 days prior, in order to provide sufficient time for the fluid waste receiver 12 to be removed, capped and shipped to the appropriate location for incineration or other permanent disposal. It is recognized that this example is provided for ease of understanding only, and is not intended to limit in any manner the time frames pertaining to usage of the indicators 36, 38. For instance, the maximum time can be greater or less than 90 days. Furthermore, activation of one of the indicators 36, 38 can occur greater than or less than 15 days prior to such expiration.

In certain embodiments, the disposal assembly 10 can include a controller 31 (illustrated, in FIG. 1C) that can be retained in the retainer base 26. The controller 31 controls and or monitors various functions of the disposal assembly 10, including the activation of the indicators 32, 34 and/or the indicators 36, 38, as non-exclusive examples. In various non-exclusive embodiments, the controller 31 can include one or more types of electronics, printed circuit boards, integrated circuits, time-keeping devices and weight detection and/or monitoring devices, as described in greater detail herein. In addition, or in the alternative, the controller 31 can include one or more power supplies, such as electrochemical cell structures (not illustrated in FIG. 1A) that may be useful in providing power to the disposal assembly 10.

Figure 1B:
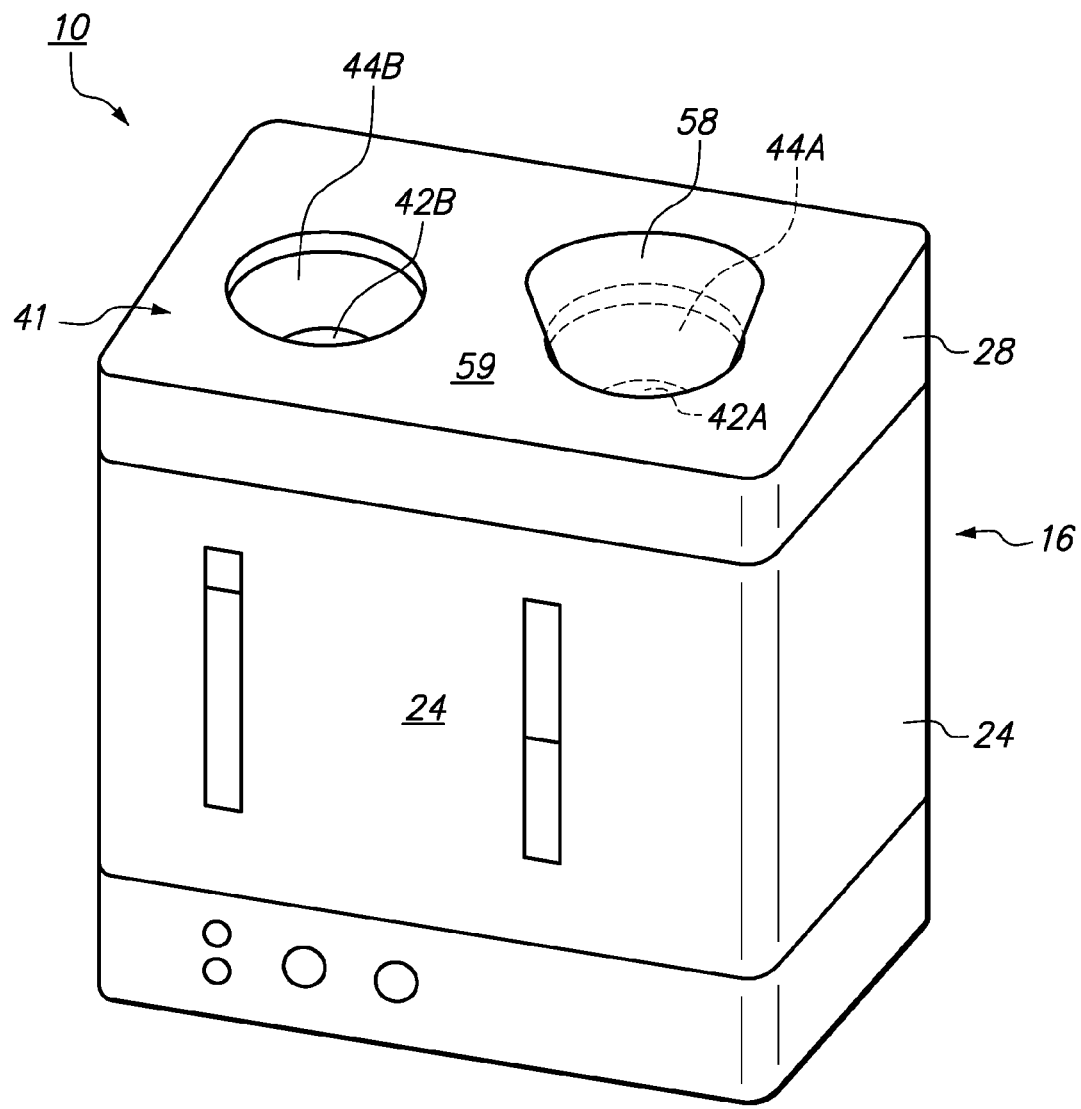
FIG. 1B is a perspective view of the pharmaceutical waste disposal assembly shown in FIG. 1A, illustrated in a closed position.

In one embodiment, the retainer lid 28 is movably secured to one of the retainer side walls 24, and can protect the contents of the retainer housing 22. Further, the retainer lid 28 selectively inhibits tampering or removal of the contents of the retainer housing 22. The retainer lid 28 can selectively be moved from the open position as illustrated in FIG. 1A to a closed position, as illustrated in FIG. 1B. The receiver retainer 16 can include a locking mechanism 1456 (illustrated in FIG. 14, for example) that allows the retainer lid 28 to be locked in place in the closed position. The retainer lid 28 can be hinged to one of the retainer side walls 24 with one or more hinges 40 (three hinges 40 are illustrated in FIG. 1A). Alternatively, other suitable structures known to those skilled in the art can movably secure the retainer lid 28 to one of the retainer side walls 24. Still alternatively, the retainer lid 28 can be completely removable from the retainer housing 22 such that the retainer lid 28 is not permanently secured to one of the retainer side walls 24.

In the embodiment illustrated in FIG. 1A, the retainer lid 28 includes an inner surface 39 and an opposing outer surface 41. The inner surface 39 is only visible when the receiver retainer 16 is in the open position, as illustrated in FIG. 1A. In this embodiment, the retainer lid 28 includes a lid top 43 and one or more lid apertures (two lid apertures 42A, 42B, are illustrated in FIG. 1A). The lid apertures 42A, 42B, allow fluid waste and/or solid waste to be deposited into one of the waste receivers 12, 14, from outside of the disposal assembly 10. In this embodiment, the lid apertures 42A, 42B, are positioned in, and extend through, the lid top 43. Alternatively, the lid apertures 42A, 42B, can be positioned on another surface of the retainer lid 28.

In one embodiment, one or more of the lid apertures 42A, 42B, can each include a waste guide 44A, 44B that assists in directing the specific phase of waste (solid, liquid or gas) to the appropriate waste receiver 12, 14. In non-exclusive embodiments, the waste guide 44A, 44B, can include a standard funnel-type device, a spiral funnel, or a series of diverters that guide the waste to the appropriate waste receiver 12, 14. The waste guides 44A, 44B, can further inhibit or prevent wrongful, illegal or unwanted extraction of waste from inside the receiver retainer 16 and/or the waste receivers 12, 14 by inhibiting or impeding hands or other objects from entering the interior of the retainer housing 22 and/or the waste receivers 12, 14 when the receiver retainer 16 is in the closed position.

The retainer housing 22 can also include one or more dividers 46 that compartmentalize the interior of the receiver retainer 16 for holding the waste receivers 12, 14, the receiver caps 18, 20, or other structures within the retainer housing 22. In the embodiment illustrated in FIG. 1A, the dividers 46 can divide the interior of the receiver retainer 16 into compartments including a fluid cap compartment 48 and a solid cap compartment 50. The receiver caps 18, 20 can be placed into their respective compartments 48, 50, in an untethered manner, or the receiver caps 18, 20, can be tethered to their respective waste receiver 12, 14, so that the receiver caps 18, 20, are not lost or otherwise inadvertently (and permanently) separated from their respective waste receivers 12, 14. Once one of the waste receivers 12, 14, is deemed to have expired, has reached a predetermined fill level, or otherwise needs to be removed from the receiver retainer 16, the corresponding receiver cap 18, 20, is positioned on the waste receiver 12, 14, for transport and/or further processing, such as by incineration as one non-exclusive example.

In the embodiment illustrated in FIG. 1A, the receiver retainer 16 also includes one or more waste receiver liners 52, 54. In this embodiment, the fluid waste receiver 12 can be positioned within a fluid waste receiver liner 52, and the solid waste receiver 14 can be positioned within a solid waste receiver liner 54. The waste receiver liners 52, 54 inhibit waste that may have been inadvertently spilled, or overflow waste, from coming into contact with the retainer housing 22, the controller 31, or other structures that may potentially be damaged by direct contact with the waste. One or more of the waste receiver liners 52, 54 can be fixedly in position within the retainer housing 22. Alternatively, one or more of the waste receiver liners 52, 54 can be removable from the retainer housing 22. Still alternatively, the waste receiver liners 52, 54 can be omitted from the receiver retainer 16.

It is important to note that in FIG. 1A and many of the other Figures, various structures are not necessary shown to scale so that all structures may be adequately represented and visualized.

FIG. 1B is a perspective view of the pharmaceutical waste disposal assembly 10 illustrated in FIG. 1A, illustrated in a closed position. In this embodiment, the outer surface 41 of the retainer lid 28 is visible, but the inner surface 39 (illustrated in FIG. 1A) is within the interior of the receiver retainer 16. Further, in this embodiment, the lid apertures 42A, 42B, and the waste guides 44A, 44B, are likewise visible and accessible from the exterior of the receiver retainer 16. In the embodiment illustrated in FIG. 1B, the receiver retainer 16 includes a fluid waste diverter 58 that diverts waste through one of the lid apertures 42A, 42B, which may otherwise not have been properly aimed at or into one of the lid apertures 42A, 42B. In this embodiment, the waste diverter 58 is positioned at least partially around the lid aperture 42A, which is designed to receive fluid waste. However, it is understood that the fluid waste diverter 58 could have also or alternatively been positioned at least partially around the lid aperture 42B to guard against errant solid waste not being received by the lid aperture 42B.

In the embodiment illustrated in FIG. 1B, the retainer lid 28 includes a top surface 59 that is substantially planar. In one embodiment, the top surface 59 can be angled toward the user to allow easier deposition of fluids and solids into the disposal assembly 10. Alternatively, the top surface 59 can be flat, i.e. perpendicular to one or more of the retainer side walls 24 (two side walls 24 are illustrated in FIG. 1B). Still alternatively, the top surface 59 can be angled away from a user, or can be angled to one side or another. In another embodiment, the top surface 59 can have a non-planar configuration, i.e. curved, multi-faceted, etc.

Figure 1C:
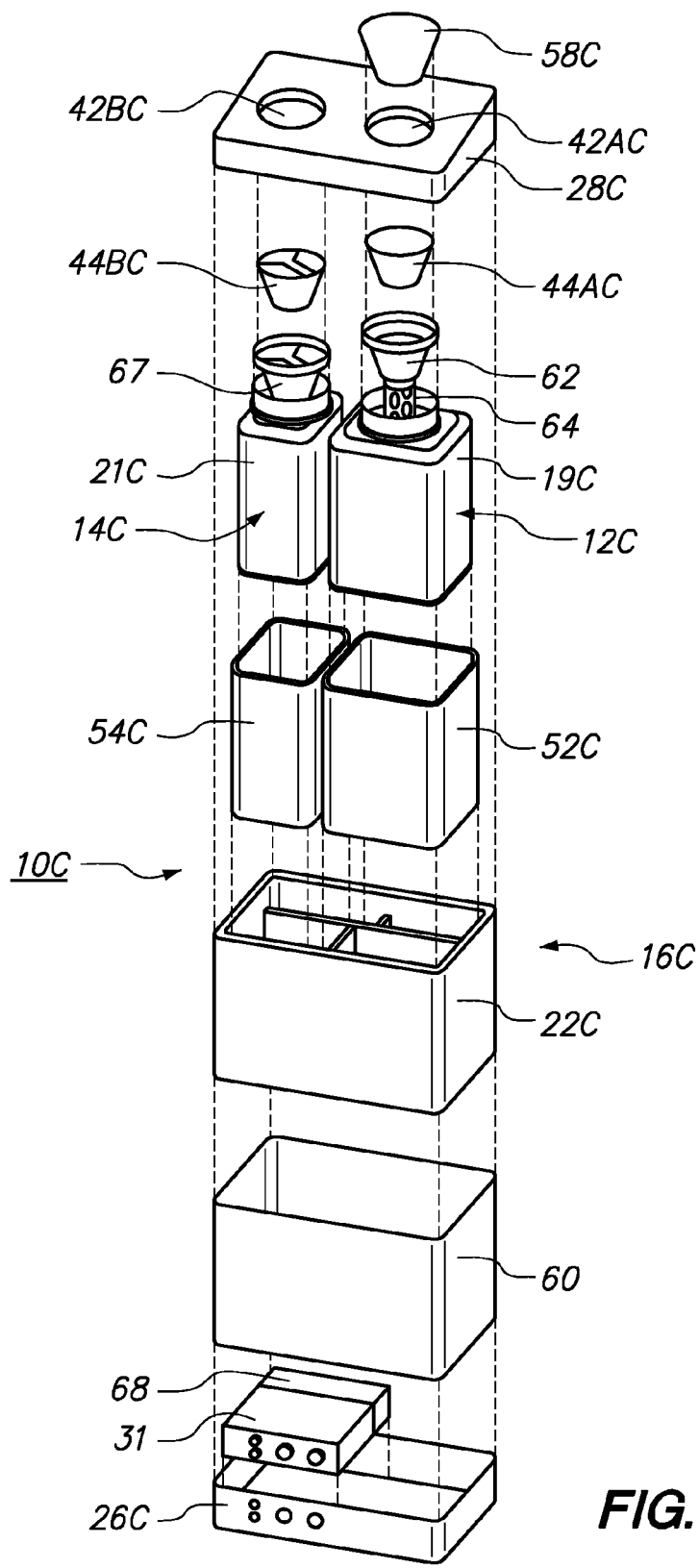
FIG. 1C is an exploded view of the pharmaceutical waste disposal assembly illustrated in FIG. 1A.

FIG. 1C is an exploded view of one embodiment of a disposal assembly 10C. In this embodiment, the disposal assembly 10C includes a fluid waste receiver 12C, a solid waste receiver 14C and a receiver retainer 16C. The positioning of the fluid waste receiver 12C and the solid waste receiver 14C relative to the receiver retainer 16C can vary from that shown in FIG. 1C. In this embodiment, the fluid waste receiver 12C includes a fluid receiver guide 62 (also sometimes referred to herein as "receiver guide") that guides the fluid waste into the fluid receiver body 19C. The fluid receiver guide 62 can include a standard funnel-type device, a spiral funnel, or a series of diverters. The fluid receiver guide 62 can further inhibit or prevent wrongful, illegal or unwanted extraction of waste from inside the fluid waste receiver 12C by inhibiting or impeding hands or other objects from entering the fluid receiver body 19C. In the embodiment illustrated in FIG. 1C, the fluid receiver guide 62 can include a fluid distributor 64 that directly distributes and/or disperses fluid to different levels within the fluid waste receiver 12C, as described in greater detail herein. Alternatively, the fluid receiver guide 62 and the fluid distributor 64 can be separate and/or spaced-apart structures within the fluid waste receiver 12C.

The solid waste receiver 14C includes a solid receiver guide 67 that guides the fluid waste into the fluid receiver body 21C. The solid receiver guide 67 can include a standard funnel-type device, a spiral funnel, or a series of diverters. The solid receiver guide 67 can further inhibit or prevent wrongful, illegal or unwanted extraction of waste from inside the solid waste receiver 14C by inhibiting or impeding hands or other objects, from entering the solid receiver body 21C.

The receiver retainer 16C includes a retainer housing 22C, a retainer base 26C, and a retainer lid 28C having a waste diverter 58C, which are substantially similar to those previously described. The disposal assembly 10C also includes a controller 31 which can control and/or monitor various functions of the disposal assembly 10C, including the activation of the indicators 32, 34 (illustrated in FIG. 1A) and/or the indicators 36, 38 (illustrated in FIG. 1A), as non-exclusive examples. In various non-exclusive embodiments, the controller 31 can include one or more types of electronics, printed circuit boards, integrated circuits, time-keeping devices and weight detection and/or monitoring devices, as described in greater detail herein. In addition, or in the alternative, the controller 31 can include one or more power supplies, such as electrochemical cell structures 68 that may be useful in providing power to the disposal assembly 10C. In one embodiment, the controller 31 can be a separate, removable structure that can be removed in the event of a malfunction, for the purpose of upgrading/updating the controller 31, to service the controller 31, or once the controller 31 reaches the end of its useful life.

In this embodiment, the retainer lid 28C includes one or more lid apertures (two lid apertures 42AC, 42BC, are illustrated in FIG. 1C). The lid apertures 42AC, 42BC function substantially in the same manner as those previously described herein, allowing fluid waste and/or solid waste to be deposited into one of the waste receivers 12C, 14C, from outside of the disposal assembly 10C. In this embodiment, the lid apertures 42AC, 42BC, are positioned in, and extend through, the lid top 43.

In the embodiment illustrated in FIG. 1C, the lid apertures 42AC, 42BC, each includes a corresponding waste guide 44AC, 44BC that assists in directing the specific phase of waste (solid, liquid or gas) to the appropriate waste receiver 12C, 14C. The waste guides 44AC, 44BC can include a standard funnel-type device, a spiral funnel, or a series of diverters that guide the waste to the appropriate waste receiver 12C, 14C, in a manner substantially similar or identical to that previously described herein.

In the embodiment illustrated in FIG. 1C, the receiver retainer 16C also includes one or more waste receiver liners 52C, 54C, described previously herein. Further, in this embodiment, the disposal assembly 10C can also include a retainer sleeve 60 that encircles at least a portion of the retainer housing 22C. The retainer sleeve 60 can be formed from various plastic materials or other synthetic materials, metal, various composites, or any other suitable materials. The sleeve can provide added sheer strength to the disposal assembly 10C and/or can provide a decorative surface that is aesthetically pleasing in a hospital or health care facility setting.

Figure 2:
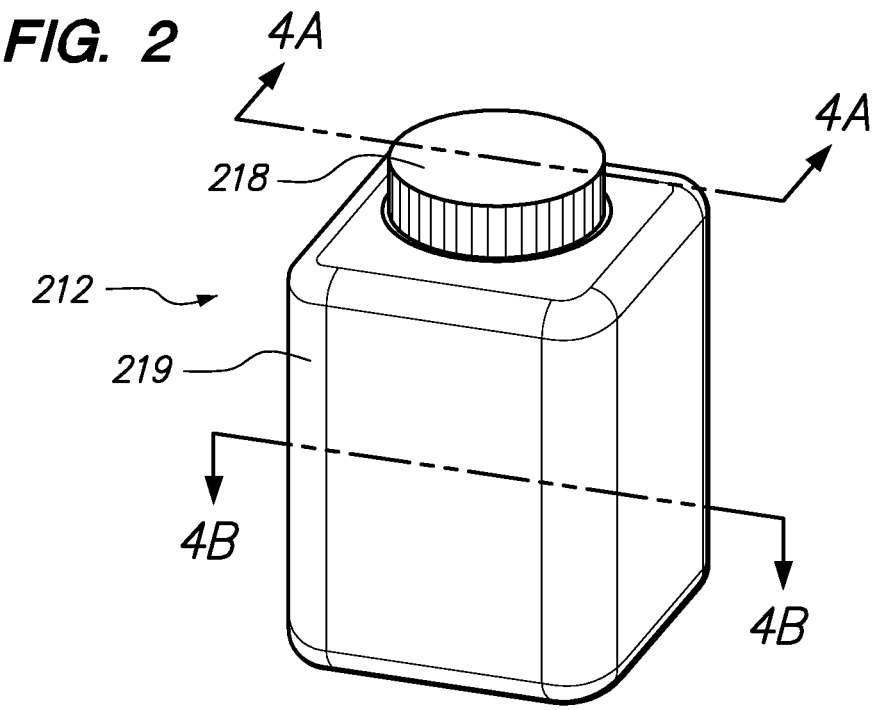
FIG. 2 is a perspective view of one embodiment of the fluid waste receiver having features of the present invention.

FIG. 2 is a perspective view of one embodiment of a fluid waste receiver 212 including the fluid receiver cap 218 and the fluid receiver body 219. The specific configuration of the fluid receiver body 219 of the fluid waste receiver 212 can vary depending upon the design requirements of the disposal assembly 10. In the embodiment illustrated in FIG. 2, the fluid receiver body 219 has a somewhat rectangular shape. Alternatively, the fluid receiver body 219 can be conical, frusto-conical, cubical, spherical, pyramidal, or can have any other suitable shape.

Figure 3:
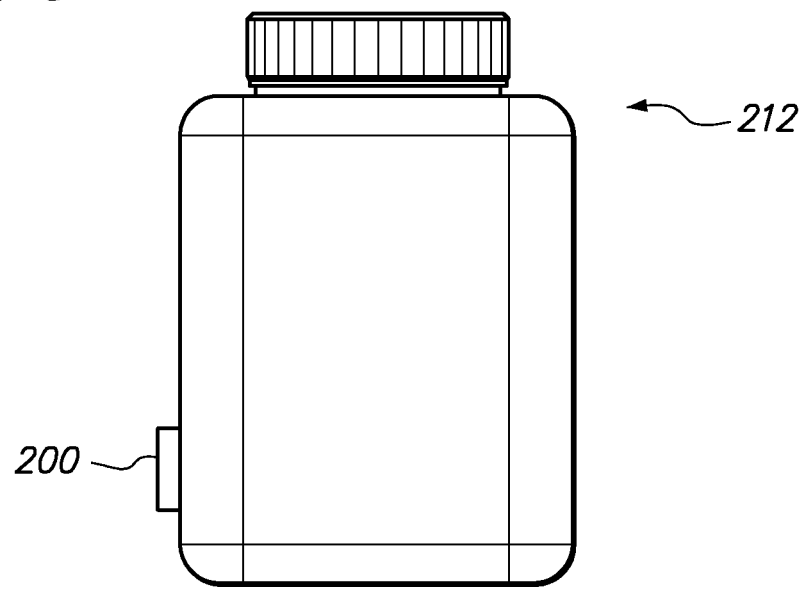
FIG. 3 is a front elevation view of the fluid waste receiver illustrated in FIG. 2.

FIG. 3 is a front elevation view of the fluid waste receiver 212 illustrated in FIG. 2. In FIG. 3, the fluid waste receiver 212 has curved, e.g., radiused, corners and edges. Additionally, in this embodiment, the fluid waste receiver 212 includes an identification tag 200. In one embodiment, the identification tag 200 can be used in conjunction with an identification reader 1500 (illustrated in FIG. 15) that is positioned on another structure of the disposal assembly 1510, such as the receiver retainer 1516 (illustrated in FIG. 15, for example), as set forth in greater detail below. In one embodiment, the identification tag 200 can be a radio frequency identification ("RFID") tag. In addition, or in the alternative, the identification tag 200 can include a barcode label, a printed serial number, an integrated circuit, and/or any other suitable type of identifier of the particular fluid waste receiver 212. In another embodiment, the identification tag 200 can be used independently of any type of identification reader such that the identification tag 200 is used as a "stand alone" identifier of the fluid waste receiver 212.

The identification tag 200 can include an active RFID tag, which can contain a battery and can transmit signals autonomously. Alternatively, the identification tag 200 can include a passive RFID tag, which can have no battery and can require an external source to provoke signal transmission. Still alternatively, the identification tag 200 can include a battery assisted passive (BAP) RFID tag, which can require an external source to wake up but have significant higher forward link capability providing greater range.

FIG. 4A is a cross-sectional view of the fluid waste receiver 212A taken on line 4A-4A in FIG. 2, with the fluid receiver cap 218 (illustrated in FIG. 2) removed for clarity. In the embodiment illustrated in FIG. 4A, the fluid waste receiver 212A includes the identification tag 200, a fluid receiver body 219, a fluid receiver guide 262, a fluid distributor 264A, a fluid absorber 270A, an absorber retainer 272, a fluid processor 274 and a fluid deodorizer 276. The fluid receiver guide 262 is substantially similar or identical to the fluid receiver guide 62 previous described herein.

In certain embodiments, the fluid distributor 264A receives fluid waste via the fluid receiver guide 262 and can directly distribute and/or allow the fluid waste to flow to one or more levels 270L, 270M, 270U of the fluid absorber 270A in a more even (e.g., non-random) manner, as illustrated by arrows 265. As used herein, the term "directly distribute" means that migration of the fluid waste from one level 270L, 270M, 270U to another is not necessary because due to its design, the fluid distributor 264A allows the fluid waste to initially enter the fluid absorber 270A at each of the levels 270L, 270M, 270U, rather than at one single level. With this design, the fluid waste can more rapidly be absorbed by the fluid absorber 270A, which inhibits puddling or ponding of fluid waste within the fluid waste receiver 212A.

Figure 4B:
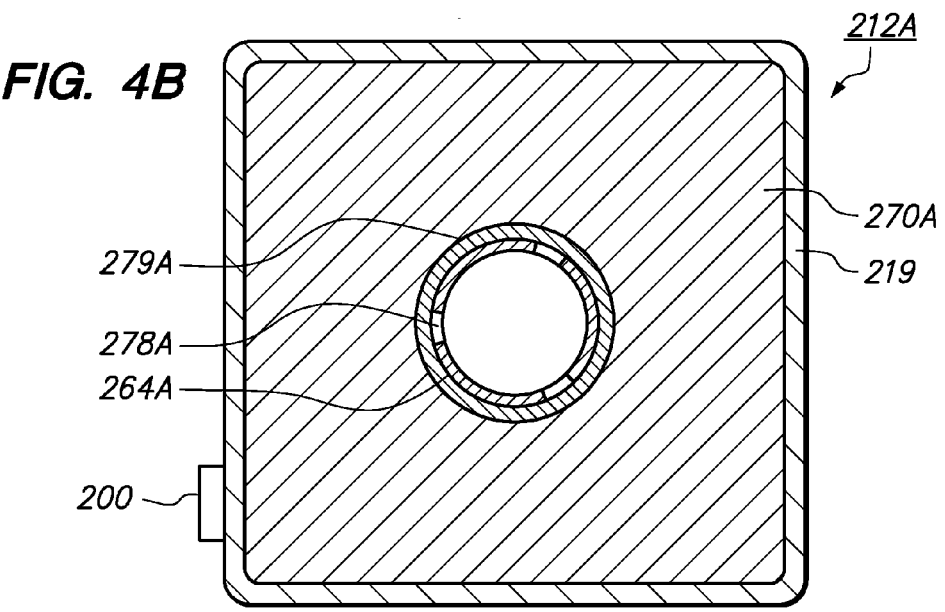
FIG. 4B is a cross-sectional view of the fluid waste receiver taken on line 4B-4B in FIG. 2.

The shape and positioning of the fluid distributor 264A relative to the fluid waste receiver 212A can vary depending upon the design requirements of the fluid waste receiver 212A. In one embodiment, the fluid distributor 264A can have a substantially tubular shape with a circular cross-section, as illustrated in FIG. 4B. Alternatively, the fluid distributor 264A can have a different shape and/or a different cross-section. In alternative non-exclusive embodiments, for example, the fluid distributor 264A can have a conical, frustoconical, pyramidal, hourglass or other suitable shape. Further, in alternative non-exclusive embodiments, the fluid distributor 264A can have an elliptical, triangular, square, hexagonal, or any other suitable polygonal or irregular cross-sectional shape in order to accomplish the desired fluid distribution of the fluid waste to the fluid absorber 270A. In one embodiment, the fluid distributor 264A can be formed from a durable plastic material. Alternatively, the fluid distributor 264A can be formed from another suitable material, such as metal, various composite materials, glass, fiberglass, ceramic, or any other relatively durable materials.

In addition, the extent to which the fluid distributor 264A extends into the fluid waste receiver 212A can vary. For example, the fluid distributor 264A need not extend all the way to a bottom of the fluid waste receiver 212A as illustrated in FIG. 4A. Stated another way, the fluid distributor 264A has a length 201A that can be varied to suit the design requirements of the fluid waste receiver 212A. In one embodiment, the fluid distributor 264A can have a shorter length 201A relative to the fluid waste receiver 212A than that illustrated in FIG. 4A.

In one embodiment, the fluid distributor 264A can include a plurality of distributor apertures 278A that enable the fluid waste to directly flow in accordance with the arrows 265 into the fluid absorber 270A at various vertical levels within the fluid waste receiver 212A. With this design, the fluid distributor 264A acts as a temporary reservoir until the fluid waste moves through the distributor apertures 278A and is at least partially or fully absorbed by the fluid absorber 270A. Further, the fluid distributor 264A can more evenly and directly distribute the fluid waste to various levels 270L, 270M, 270U of the fluid absorber 270A, i.e. a lower level 270L, a middle level 270M and an upper level 270U of the fluid absorber 270A. Stated another way, the fluid distributor 264A inhibits any one level 270L, 270M, 270U within the fluid absorber 270A from having to absorb substantially more fluid waste than any other level 270L, 270M, 270U. Further, the fluid distributor 264A can inhibit the fluid waste from simply collecting on the upper level 270U of the fluid absorber 270A. Because the fluid distributor 264A extends through at least a portion of the fluid absorber 270A, the fluid waste does not need to diffuse through the upper level 270U to reach the middle and lower levels 270M, 270L, resulting in more rapid absorption of the fluid waste by the fluid absorber 270A.

As used herein, the term "levels" of the fluid absorber 270A refers to vertical levels that have relative positioning within the fluid receiver body 219. For example, the lower level 270L is positioned adjacent to and/or near a receiver bottom 283 (illustrated in FIG. 4C). The upper level 270U is positioned furthest away from the receiver bottom 283, e.g., in one embodiment, adjacent to or near the absorber retainer 272. The middle level 270M is positioned between the lower level 270L and the upper level 270U. In the embodiment illustrated in FIG. 4A, the fluid distributor 264A extends downwardly from the fluid receiver guide 262 at least partially, if not fully, through the various levels 270L, 270M, 270U of the fluid absorber 270A.

The size, shape, density and number of distributor apertures 278A can vary depending upon the requirements of the fluid waste receiver 212A and/or the shape and/or size of the fluid absorber 270A, and/or the material used to form the fluid absorber 270A. In one embodiment, all of the distributor apertures 278A are substantially similar in size and/or shape. In another embodiment, the sizes of the distributor apertures 278A can be different depending upon their location on the fluid distributor 264A. In still another embodiment, the density of distributor apertures 278A can be substantially similar over the length 201A of the fluid distributor 264A. Alternatively, the density of distributor apertures 278A can vary over the length 201A of the fluid distributor 264A. The foregoing embodiments are provided as examples only, and are not intended to be limiting in any manner. For example, in another embodiment, one fluid distributor 264A can combine varying sizes, shapes and densities of distributor apertures 278A.

In one embodiment, the fluid distributor 264A can include a distributor sleeve 279A that inhibits any portion of the fluid absorber 270A from entering into the fluid distributor 264A through any of the distributor apertures 278A. The distributor sleeve 279A can include a fluid-permeable material that wraps partially or fully around the fluid distributor 264A to act as a fluid-permeable barrier between a distributor interior 277A of the fluid distributor 264A and the portion of the fluid receiver body 219 that contains the fluid absorber 270A. Importantly, the distributor sleeve 279A does not unduly impede fluid flow from the distributor interior 277A of the fluid distributor 264A out through the distributor apertures 278A and into the fluid absorber 270A. In one embodiment, the distributor sleeve 279A can be formed from a material such as a durable fabric-type material. Alternatively, the distributor sleeve 279A can be formed from a plastic material, or any other suitably durable, yet fluid-permeable, material.

The fluid absorber 270A absorbs fluid waste that enters the fluid distributor 264A. In one embodiment, the fluid absorber 270A includes a solid material such as a super absorbent polymer (SAP), which can also be combined with additional fluff or fibrous materials, for example. Alternatively, the fluid absorber 270A can include other suitable, relatively absorbent materials. The material that forms the fluid absorber 270A can also include antibacterial, antimicrobial, and/or anti-odor characteristics. In one embodiment, the fluid absorber 270A can be impregnated with a silver or copper type of antibacterial and/or antimicrobial agent to reduce or eliminate the possibility of bacterial or fungal growth. In one embodiment, the fluid absorber 270A can convert the fluid waste to a gelatinous or solid material that is less likely to spill or leak from the fluid waste receiver 212A.

The absorber retainer 272 maintains the positioning of the fluid absorber 270A within the fluid waste receiver 212A. In one embodiment, the absorber retainer 272 can include a fluid-permeable screen, such as a plastic or wire mesh screen. Alternatively, the absorber retainer 272 can be a substantially fluid-impermeable layer. By maintaining the position of the fluid absorber 270A, the absorber retainer 272 also maintains an gap region 280 within the fluid waste receiver 212A, and acts as a fluid permeable barrier between the fluid absorber 270A and the gap region 280. Additionally, the gap region 280 acts as an overflow reservoir that holds unabsorbed fluid waste, if necessary, until the fluid waste can be absorbed by the fluid absorber 270A.

The fluid processor 274 can process the fluid waste in one or more ways. For example, the fluid processor 274 can include a deodorizer, an antimicrobial agent, an antibacterial agent and/or an antifungal agent. The fluid processor 274 can also include an upper solid waste filter 282U and/or a lower solid waste filter 282L that inhibit or prevent solid waste, such as pills, capsules, syringes, needles, etc., or portions thereof, or particles from the fluid processor 274 from entering into the fluid distributor 264A. Further, in certain embodiments, the solid waste filters 282U, 282L can act as an additional barrier to inhibit or prevent portions of the fluid absorber 270A from exiting the fluid waste receiver 212 in the event the fluid waste receiver is inverted. The solid waste filters 282U, 282L can include a screen or mesh material, or another suitable fluid-permeable structure.

The fluid deodorizer 276 deodorizes the fluid waste that enters the fluid waste receiver 212A. In the embodiment illustrated in FIG. 4A, the fluid deodorizer 276 is secured to an upper portion of the fluid receiver body 219 with one or more deodorizer fasteners 284. The fasteners 284 can include pins, screws, or any other suitable fasteners. It is understood that in other embodiments, the fluid deodorizer 276 can be positioned in other locations within the fluid waste receiver 212A, and that the example provided in FIG. 4A is only provided as one workable position for the fluid deodorizer 276, and is not intended to limit the invention in any manner. In one embodiment, the fluid deodorizer 276 can be somewhat similar to the material that forms the fluid processor 274. In non-exclusive alternative embodiments, the fluid deodorizer 276 can include a carbon-based filter, a scented deodorizer, or another suitable structure that performs the intended function of deodorizing the interior of the fluid receiver body 219.

FIG. 4B is a cross-sectional view of the fluid waste receiver 212A taken on line 4B-4B in FIG. 2. In this embodiment, the fluid distributor 264A is substantially centrally positioned within the fluid receiver body 219. In an alternative embodiment, the fluid distributor 264A can be positioned off-center within the fluid receiver body 219. Still alternatively, the fluid distributor 264 can include greater than one tubular (or other shaped) section that extends into the fluid absorber 270A. Stated another way, the fluid distributor 264A can have a plurality of distributor branches (such as those illustrated in FIG. 4K, for example) that extend into the fluid absorber 270A. In the embodiment illustrated in FIG. 4B, the fluid absorber 270A encircles or surrounds the fluid distributor 264A to substantially fill a space between the fluid receiver body 219 and the distributor sleeve 279A of the fluid distributor 264A. In an alternative embodiment, there may be voids or gaps between the fluid absorber 270A and the fluid receiver body 219. In the embodiment illustrated in FIG. 4B, the distributor apertures 278A are positioned at various points around the circumference of the fluid distributor 264A. It is understood, however, that the positioning of distributor apertures 278A can vary from that illustrated in FIG. 4B.

Figure 4C:
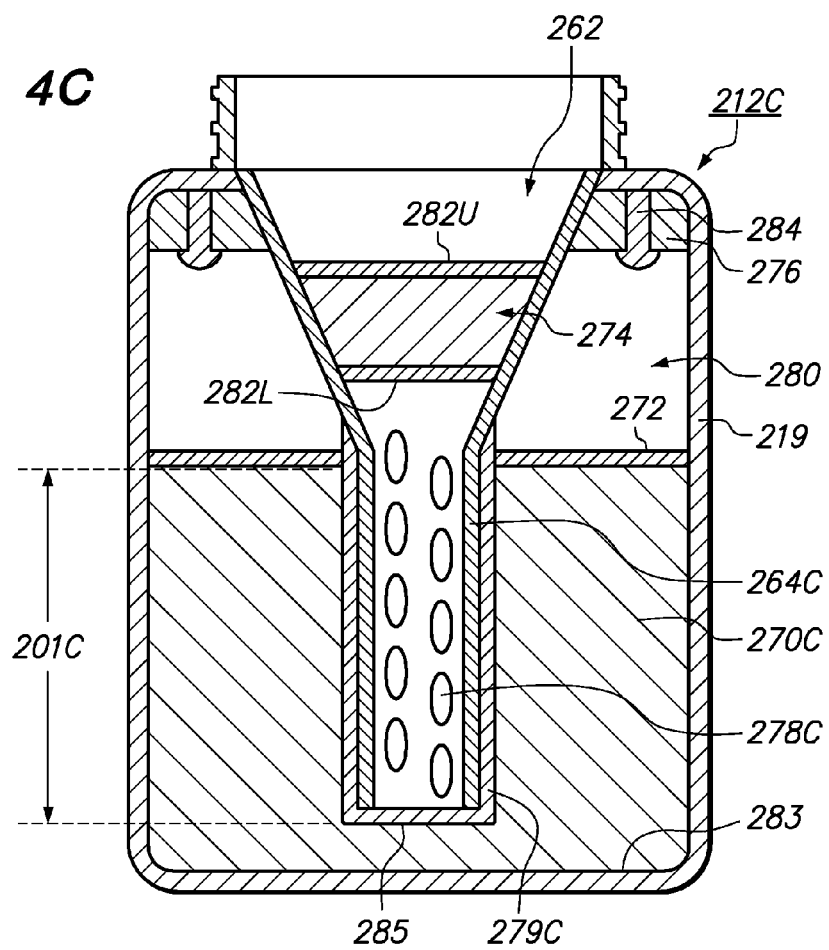
FIG. 4C is a cross-sectional view of a portion of another embodiment of the fluid waste receiver.

FIG. 4C is a cross-sectional view of a portion of another embodiment of the fluid waste receiver 212C. In this embodiment, the fluid waste receiver 212C is substantially similar to the fluid waste receiver 212A illustrated in FIG. 5A, except for certain modifications noted herein. So as not to obscure the features described relative to FIG. 4C, many of the features of the fluid waste receiver 212A illustrated in FIG. 4A have been omitted from FIG. 4C.

In the embodiment illustrated in FIG. 4C, the fluid receiver 212C includes a receiver bottom 283 that supports the fluid absorber 270C. In this embodiment, the fluid distributor 264C extends from the fluid receiver guide 262 to a point above the receiver bottom 283. Stated another way, the fluid distributor 264C does not extend all the way to the receiver bottom 283, but stops short of the receiver bottom 283. With this design, fluid waste can not only migrate out of the distributor apertures 278C into the fluid absorber 270C, but the fluid waste can also migrate out of the fluid distributor 264C through a distributor bottom 285 of the fluid distributor 264C. In one embodiment, the distributor bottom 285 can be partially or completely open, with the exception of the distributor sleeve 279C which may cover some or the entire distributor bottom 285 in a fluid-permeable manner. Therefore, in one embodiment, the distributor sleeve 279C can inhibit or prevent the material that forms the fluid absorber 270C from migrating in an upwardly direction into the fluid distributor 264C.

Figure 4D:
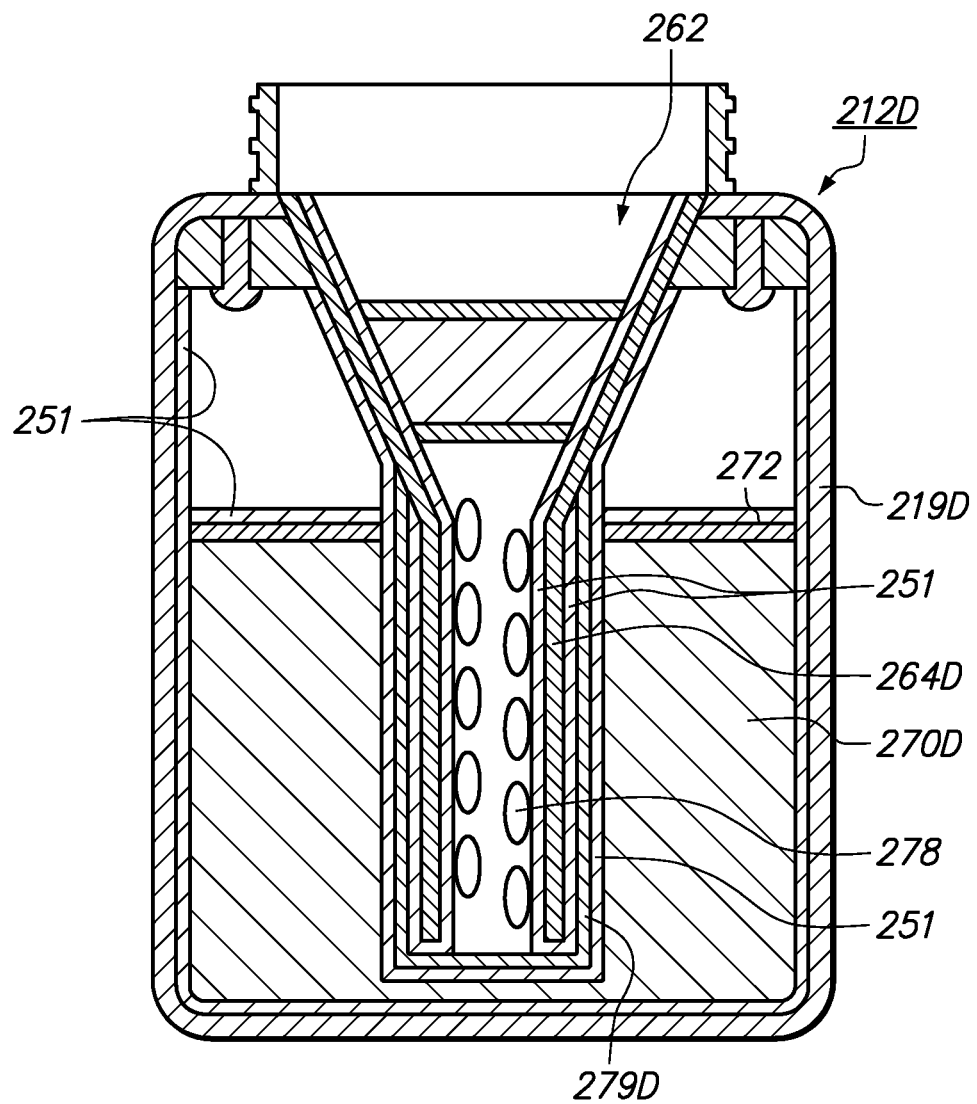
FIG. 4D is a cross-sectional view of a portion of yet another embodiment of the fluid waste receiver.

FIG. 4D is a cross-sectional view of a portion of yet another embodiment of the fluid waste receiver 212D. In this embodiment, the fluid waste receiver 212D includes an antimicrobial layer 251 that thinly coats at least portions of one or more structures within the fluid waste receiver 212D. For example, in the embodiment illustrated in FIG. 4D, the antimicrobial layer 251 can be positioned on one or more surfaces of the fluid receiver body 219, the fluid distributor 264D, the absorber retainer 272, the distributor sleeve 279D, and/or any other suitable surface within the fluid waste receiver 212D. In one non-exclusive embodiment, the antimicrobial layer 251 can be formed from materials that can disrupt the ability of germs and other bacteria from adhering to or reproducing on surfaces of the fluid waste receiver 212D. However, it is recognized that any suitable antimicrobial agent known to those skilled in the art can be used to form the antimicrobial layer 251. Further, the thickness of the antimicrobial layer 251 can vary as required to suit the design requirements of the fluid waste receiver 212D based on knowledge of those skilled in the art. In one embodiment, the thickness of the antimicrobial layer 251 can be one micron or less. Alternatively, the thickness of the antimicrobial layer 251 can be within the range of 1-500 microns, or greater.

FIG. 4E is a cross-sectional view of another embodiment of a portion of the fluid waste receiver 212E, including the fluid receiver guide 262E and the fluid distributor 264E. In this embodiment, the fluid distributor 264E includes a plurality of substantially oval or elliptical distributor apertures 278E that increase in size along the length 201E of the fluid distributor 264E in the direction from the fluid receiver guide 262E toward the distributor bottom 285E. With this design, a greater volume of the fluid waste is directed toward the lower level 270L (illustrated in FIG. 4A) of the fluid absorber 270A (illustrated in FIG. 4A, for example), and a lesser volume is directed toward the upper level 270U (illustrated in FIG. 4A) of the fluid absorber 270A. Although in this embodiment, the distributor apertures 278E are shown as being substantially evenly spaced and similar in shape, it is understood that the distributor apertures 278E can be dissimilar in shape and/or unevenly spaced, and/or can have a different shape than that illustrated in FIG. 4E. In an alternative embodiment (not shown), the distributor apertures 278E can decrease in size along the length 201E of the fluid distributor 264E in the direction from the fluid receiver guide 262E toward the distributor bottom 285E.

FIG. 4F is a cross-sectional view of another embodiment of a portion of the fluid waste receiver 212F, including the fluid receiver guide 262F and the fluid distributor 264F. In this embodiment, the fluid distributor 264F includes a plurality of substantially slit-shaped distributor apertures 278F that are substantially similar in size, but are more dense, e.g., more numerous, in the direction from the fluid receiver guide 262F toward the distributor bottom 285F. Stated another way, a spacing between the distributor apertures 278F along a direction along the length 201F of the fluid distributor 264F is non-uniform. With this design, a greater volume of the fluid waste is directed toward the lower level 270L (illustrated in FIG. 4A) of the fluid absorber 270A (illustrated in FIG. 4A, for example), and a lesser volume is directed toward the upper level 270U (illustrated in FIG. 4A) of the fluid absorber 270A. In an alternative embodiment (not shown), the distributor apertures 278F are less dense, e.g., less numerous, in the direction from the fluid receiver guide 262F toward the distributor bottom 285F.

FIG. 4G is a cross-sectional view of another embodiment of a portion of the fluid waste receiver 212G, including the fluid receiver guide 262G and the fluid distributor 264G. In this embodiment, the fluid distributor 264G includes a plurality of relatively small distributor apertures 278G that are substantially uniform in size over the length 201G of the fluid distributor 264G. In this embodiment, the fluid distributor 264G can include a screen-like material that forms the distributor apertures 278G. The distributor apertures 278G can be any suitable size that can allow passage of fluid waste out of the fluid distributor 264G and into the fluid absorber 270A (illustrated in FIG. 4A, for example).

FIG. 4H is a cross-sectional view of another embodiment of a portion of the fluid waste receiver 212H, including the fluid receiver guide 262H and the fluid distributor 264H. In this embodiment, the fluid distributor 264H includes a plurality of distributor apertures 278H that increase in number along the length 201H of the fluid distributor 264H in the direction from the fluid receiver guide 262H toward the distributor bottom 285H. Stated another way, a density of the distributor apertures 278H is non-uniform in a direction along the length 201H of the fluid distributor 264H. With this design, a greater volume of the fluid waste is directed toward the lower level 270L (illustrated in FIG. 4A) of the fluid absorber 270A (illustrated in FIG. 4A, for example), and a lesser volume is directed toward the upper level 270U (illustrated in FIG. 4A) of the fluid absorber 270A. In an alternative embodiment (not shown), the distributor apertures 278H can decrease in number along the length 201H of the fluid distributor 264H in the direction from the fluid receiver guide 262H toward the distributor bottom 285H.

FIG. 4I is a cross-sectional view of another embodiment of a portion of the fluid waste receiver 212I, including the fluid receiver guide 262I and the fluid distributor 264I. In this embodiment, the fluid distributor 264I flares out along the length 201I of the fluid distributor 264I in a direction from the fluid receiver guide 262I toward the distributor bottom 285I. Stated another way, the fluid distributor 264I has an increasingly larger cross-sectional area moving from an upper portion 265UI toward a lower portion 265LI of the fluid distributor 264I. In addition, the fluid distributor 264I can include greater number of distributor apertures 278I along the length 201I of the fluid distributor 264I moving from the upper portion 265UI toward the lower portion 265LI of the fluid distributor 264I. With this design, a greater volume of the fluid waste is directed toward the lower level 270L (illustrated in FIG. 4A) of the fluid absorber 270A (illustrated in FIG. 4A, for example), and a lesser volume is directed toward the upper level 270U (illustrated in FIG. 4A) of the fluid absorber 270A.

FIG. 4J is a cross-sectional view of another embodiment of a portion of the fluid waste receiver 212J, including the fluid receiver guide 262J and the fluid distributor 264J. In this embodiment, the fluid distributor 264J includes a plurality of distributor apertures 278J that are substantially similar to those previously described relative to FIG. 4G. However, in this embodiment, the fluid distributor 264J flares out along the length 201J of the fluid distributor 264J moving from an upper portion 265UJ toward a lower portion 265LJ of the fluid distributor 264J, somewhat similarly to the embodiment described relative to FIG. 4I. With this design, a greater volume of the fluid waste is directed toward the lower level 270L (illustrated in FIG. 4A) of the fluid absorber 270A (illustrated in FIG. 4A, for example), and a lesser volume is directed toward the upper level 270U (illustrated in FIG. 4A) of the fluid absorber 270A.

Figure 4K:
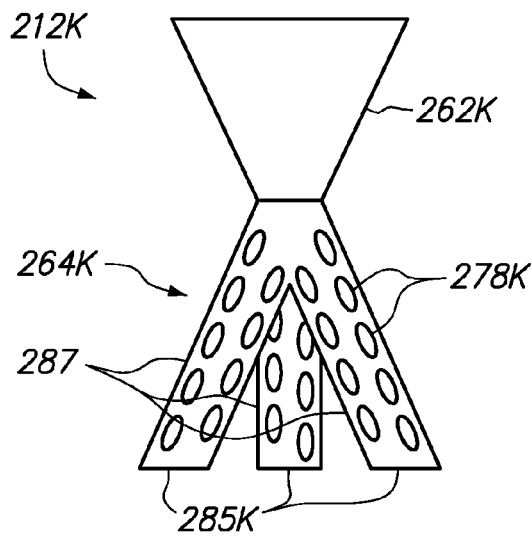
FIG. 4K is a side view of another embodiment of a portion of the fluid waste receiver.

FIG. 4K is a side view of another embodiment of a portion of the fluid waste receiver 212K, including the fluid receiver guide 262K and the fluid distributor 264K. In this embodiment, the fluid distributor 264K includes a plurality of distributor legs 287. In the embodiment illustrated in FIG. 4K, the fluid distributor 264K includes three distributor legs 287. However, in alternative embodiments, the fluid distributor 264K can include fewer than three or greater than three distributor legs 287. With this design, a greater and more evenly distributed surface area of the fluid absorber 270 (illustrated in FIG. 4A) can be directly accessible to the fluid waste exiting the fluid distributor 264K via the distributor apertures 278K. In one embodiment, fluid waste can also emanate from the fluid distributor 264K via the distributor bottom 285K of one or more of the distributor legs 287. In one embodiment, the distributor legs 287 can have a substantially similar length to one another. Alternatively, the distributor legs 287 can have different lengths from one another.

Figure 5A:
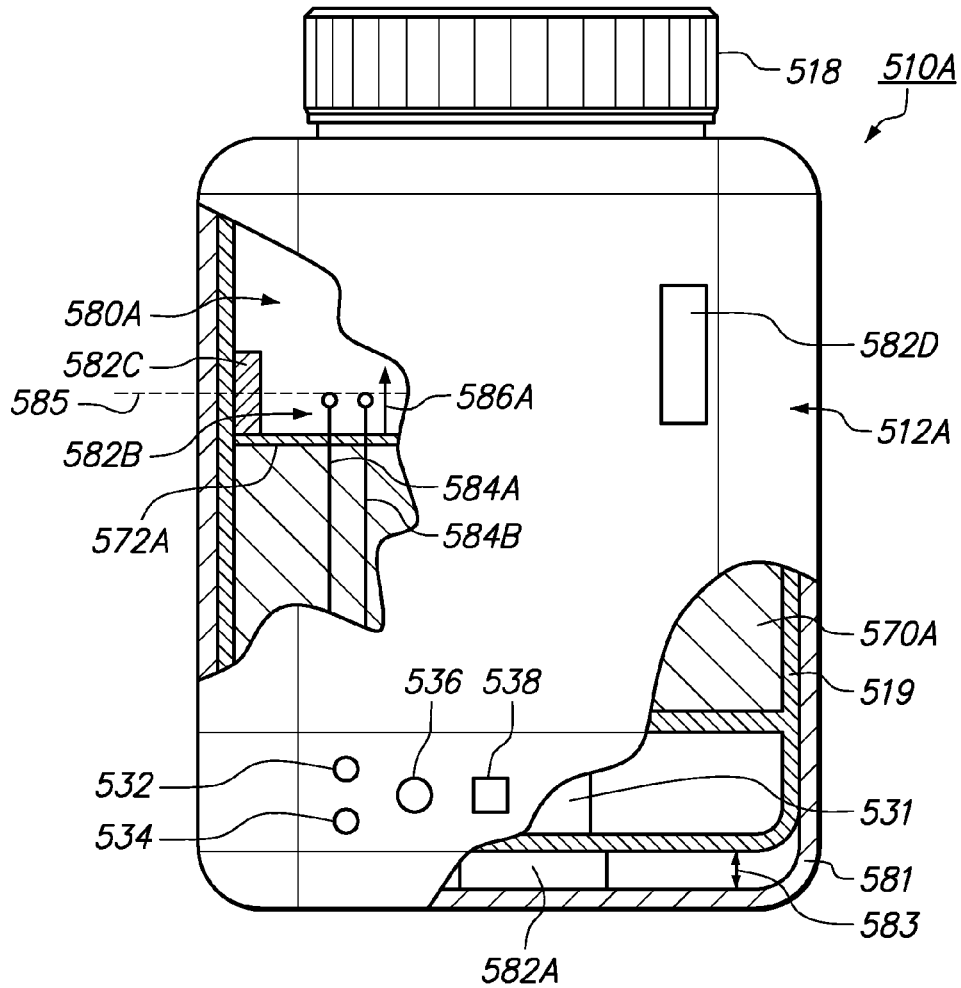
FIG. 5A is a partial cutaway view of another embodiment of the pharmaceutical waste disposal assembly having features of the present invention.

FIG. 5A is a partial cutaway view of another embodiment of a disposal assembly 510A including a fluid waste receiver 512A. In this embodiment, the fluid waste receiver 512A is fully self-contained and is not used in conjunction with a separate receiver retainer (such as receiver retainer 16 illustrated in FIG. 1A). Although not necessarily illustrated in FIG. 5A, the fluid waste receiver 512A can include some or all of the same components illustrated and described relative to FIGS. 2, 4A and 4B, including one or more of the fluid receiver guide 262, the fluid distributor 264, the fluid processor 274 and the fluid deodorizer 276, which function substantially as described previously herein.

Additionally, in the embodiment illustrated in FIG. 5A, the disposal assembly 510A includes a fluid receiver cap 518, a fluid receiver body 519, a controller 531, a charged battery indicator 532, a low battery indicator 534, a fluid waste receiver indicator 536, a fluid absorber 570A, an absorber retainer 572A, and an gap region 580A, which function substantially as previously described herein, with the exception of certain modifications provided below. Further, the disposal assembly 510A can also include a timer activator 538, a fluid receiver body retainer 581 and one or more fluid waste receiver sensors 582A, 582B, 582C, 582D.

In one embodiment, the fluid receiver body 519 is positioned within and is movable relative to the fluid receiver body retainer 581 in a direction illustrated by arrow 583. Movement of the fluid receiver body 519 relative to the fluid receiver body retainer 581 only needs to be slight, and is dependent upon the weight of the contents of the fluid receiver body 519, including any fluid waste which may be present within the fluid receiver body 519. In the embodiment illustrated in FIG. 5A, a fluid waste receiver sensor 582A is positioned between the fluid receiver body 519 and the fluid receiver body retainer 581. In one embodiment, the fluid waste receiver sensor 582A is a weight sensor, such as a load cell, for example. In this embodiment, as the weight of the fluid receiver body 519 and its contents increases, a greater force is exerted on the weight sensor 582A.

In one embodiment, the weight sensor 582A can convert a predetermined force into an electrical signal, which causes the fluid waste receiver indicator 536 to activate. Activation of the fluid waste receiver indicator 536 can alert a user that the fluid waste has reached a predetermined percentage of the capacity of the fluid receiver body 519, and the user has a certain predetermined time period to place the fluid receiver cap 518 on the fluid receiver body 519, which prepares the disposal assembly 510A for disposal. In various embodiments, the predetermined force required to activate the fluid waste receiver indicator 536 and/or the predetermined percentage of the capacity of the fluid receiver body 519 can be determined based upon various requirements of the specific regulations governing disposal of waste. Alternatively, the predetermined force required to activate the fluid waste receiver indicator 536 and/or the predetermined percentage of the capacity of the fluid receiver body 519 can be determined by the user, and can be programmed into the controller 531.

In one embodiment, the fluid waste receiver indicator 536 can be activated by the fluid waste receiver sensor 582B. In this embodiment, the fluid waste receiver sensor 582B includes two or more electrical conductors 584A, 584B that form a circuit once the liquid waste has reached a predetermined height (indicated by dashed line 585) within the fluid receiver body 519. Once the circuit has been formed, the fluid waste receiver sensor 582B sends an electrical signal to the controller 531, which then activates the fluid waste receiver indicator 536 to alert a user that the fluid waste has reached a predetermined percentage of the capacity of the fluid receiver body 519. At this point, in one embodiment, the user would have a certain predetermined time period to place the fluid receiver cap 518 on the fluid receiver body 519, which prepares the disposal assembly 510A for disposal.

In another embodiment, the fluid waste receiver indicator 536 can be activated by the fluid waste receiver sensor 582C. In this embodiment, as the fluid absorber 570A expands once a particular amount of fluid waste has been absorbed by the fluid absorber 570A, the absorber retainer 572A will move in an upward direction as indicated by arrow 586A. This upward movement generates a force against the fluid waste receiver sensor 582C. Once a predetermined force has been achieved, the fluid waste receiver sensor 582C transmits an electrical signal to the controller 531. The controller 531 then activates the fluid waste receiver indicator 536 to alert a user that the fluid waste has reached a predetermined percentage of the capacity of the fluid receiver body 519. At this point, in one embodiment, the user has a certain predetermined time period to place the fluid receiver cap 518 on the fluid receiver body 519, which prepares the disposal assembly 510A for disposal.

In this embodiment, the specific type of fluid waste receiver sensor 582C can vary. In one embodiment, the fluid waste receiver sensor 582C can be a load cell. Alternatively, the fluid waste receiver sensor 582C can include one or more piezoelectric elements. Still alternatively, other types of sensors can be used that can transmit an electrical signal based on mechanical movement of the absorber retainer 572A.

In one embodiment, the fluid waste receiver sensor 582D can be a moisture-sensitive visual indicator that changes color (e.g., white to red) once the fluid level has risen to the level of the fluid waste receiver sensor 582D. For example, in one embodiment, the fluid waste receiver sensor 582D can be positioned at a specific level that, upon a color change of the fluid waste receiver sensor 582D, would indicate the fluid waste has reached a predetermined percentage of the capacity of the fluid receiver body 519. At this point, in one embodiment, the user would have a certain predetermined time period to place the fluid receiver cap 518 on the fluid receiver body 519, which prepares the disposal assembly 510A for disposal.

The timer activator 538 activates a timer within the controller 531. The positioning of the timer activator on or within the fluid waste receiver 512A can vary to suit the design requirements of the disposal assembly 510A and/or the fluid waste receiver 512A. In one embodiment, the timer activator 538 starts a timer, such as a clock as one non-exclusive example, that tracks the time until expiration of the fluid waste receiver 512A. The timer can be included as part of and/or embedded within the controller 531. Alternatively, the timer can be separate from the controller 531, and can be maintained either within the fluid waste receiver 512A or remotely, outside of the fluid waste receiver 512A. In certain alternative embodiments, the timer can be wirelessly connected or hardwired to the timer activator 538. In one embodiment, the timer activator 538 can be manually activated by the user once usage of the disposal assembly 510A has commenced, such as by manually depressing a button, flipping a switch, or by another suitable manual method. In an alternative embodiment, the timer activator 538 can be automatically activated by some specific initiating event, such as removal of the receiver lid 518, initial addition of fluid waste or other fluid within the fluid waste receiver 512A, or some other suitable initiating event.

In one embodiment, once a predetermined period of time has elapsed following activation of the timer activator 538, the controller 531 activates the fluid waste receiver indicator 536 or a separate timer indicator (not shown), which alerts the user that a specific time period has passed, and that the useful life of the disposal assembly 510A has either expired, or that expiration is scheduled to occur in a predetermined time period. For example, if expiration of the disposal assembly 510A occurs at 90 days from activation of the timer activator 538, the controller 531 may activate the fluid waste receiver indicator 536 at 75 days to provide a 15-day lead time for the user to terminate usage of the disposal assembly 510A. It is understood that the foregoing example is provided for ease of understanding only, and is not intended to limit in any manner the time periods for which the invention may be used.

Figure 5B:
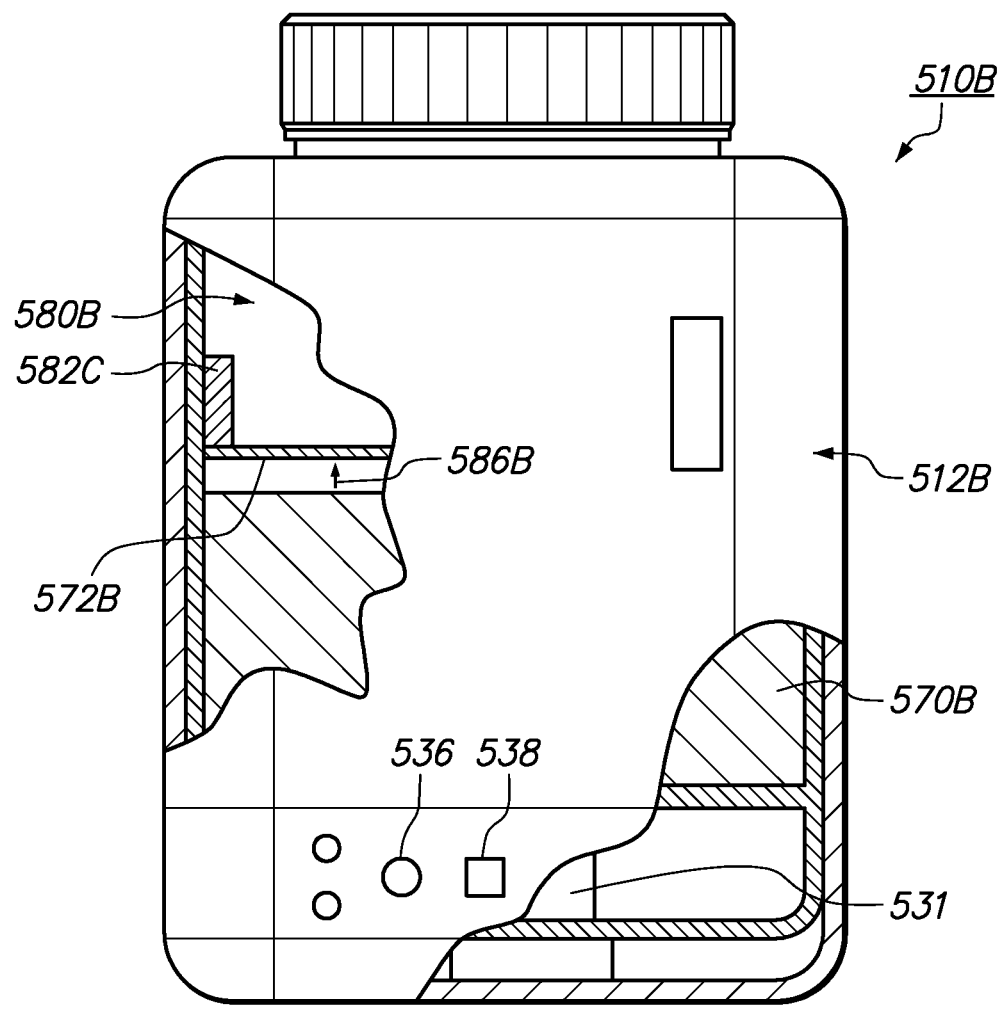
FIG. 5B is a partial cutaway view of yet another embodiment of the pharmaceutical waste disposal assembly.

FIG. 5B is a partial cutaway view of another embodiment of a disposal assembly 510B including a fluid waste receiver 512B. In this embodiment, the fluid waste receiver 512B is substantially similar to the fluid waste receiver 512A illustrated in FIG. 5A, except for certain modifications noted herein. So as not to obscure the features described relative to FIG. 5B, many of the features of the fluid waste receiver 512A illustrated in FIG. 5A have been omitted from FIG. 5B.

In the embodiment illustrated in FIG. 5B, the fluid waste receiver indicator 536 can be activated by the fluid waste receiver sensor 582C in a somewhat similar manner as that previously described. However, in this embodiment, the fluid absorber 570B is spaced apart a predetermined distance from the absorber retainer 572B to allow for a certain degree of expansion of the fluid absorber 570B as fluid waste is absorbed thereby. The specific distance that the absorber retainer 572B is spaced apart from the fluid absorber 570B can vary, but is dependent upon the specific expansion properties of the fluid absorber 570B.

Thus, once a particular amount of fluid waste has been introduced into the fluid absorber 570B, the fluid absorber 570B expands sufficiently toward the absorber retainer 572B so that the fluid absorber 570B eventually contacts the absorber retainer 572B. Therefore, in this embodiment, the fluid absorber 570B will move in an upward direction as indicated by arrow 586A as the fluid absorber 570B absorbs fluid waste. This upward movement generates a force against the fluid waste receiver sensor 582C, which in this embodiment is positioned in the gap region 580B. Once a predetermined force has been achieved, the fluid waste receiver sensor 582C transmits an electrical signal to the controller 531. The controller 531 then activates the fluid waste receiver indicator 536 to alert a user that the fluid waste has reached a predetermined percentage of the capacity of the fluid receiver body 519. At this point, in one embodiment, the user has a certain predetermined time period to place and/or lock the fluid receiver cap 518 on the fluid receiver body 519, which prepares the disposal assembly 510A for permanent disposal.

FIG. 6 is a perspective view of one embodiment of the solid waste receiver 614 including the solid receiver cap 620 and the solid receiver body 621. The specific configuration of the solid receiver body 621 of the solid waste receiver 614 can vary depending upon the design requirements of the disposal assembly 10. In the embodiment illustrated in FIG. 6, the solid receiver body 621 has a somewhat rectangular shape. Alternatively, the solid receiver body 621 can be conical, frustoconical, cubical, spherical, pyramidal, or can have any other suitable configuration.

FIG. 7 is a front elevation view of the solid waste receiver 614 illustrated in FIG. 6. In FIG. 7, the solid waste receiver 614 has curved, e.g., radiused, corners and edges.

FIG. 8A is a cross-sectional view of the solid waste receiver 614 taken on line 8-8 in FIG. 6, with the solid receiver cap 620 (illustrated in FIG. 6) removed for clarity. In the embodiment illustrated in FIG. 8A, the solid waste receiver 614 can include one or more of a solid receiver body 621, a solid receiver guide 667A, a fluid absorber 670, a reaction agent 687 and an adherer 688.

In one embodiment, the solid receiver guide 667A can include one or more solid waste diverters 658 that divert the direction of the solid waste while the solid waste is entering an interior of the solid waste receiver 614. In one embodiment, the solid waste diverters 658 can cause the solid waste to move in a back and forth or zigzag manner as the solid waste moves downward into the solid receiver body 621. In another embodiment, the solid waste diverter 658 can be in the shape of a spiral, e.g., similar to a snail shell, so that the solid waste spirals into the solid receiver body 621. Still alternatively, the one or more solid waste diverters 658 can have a different configuration. In certain embodiments, the solid waste diverters 658 can inhibit or prevent wrongful, illegal or unwanted removal of solid waste from inside solid receiver body 621 by inhibiting or impeding hands or other objects from entering the solid receiver body 621.

In this embodiment, the solid receiver guide 667A is illustrated as including two solid waste diverters 658 that guide the solid waste in a plurality of directions away from and toward the solid body access 621BA. In particular, as illustrated, the solid waste can contact the uppermost solid waste diverter 658 which guides and/or diverts the solid waste in a first direction 695A away from the solid body access 621BA. The solid waste can further contact the lower solid waste diverter 658 which guides and/or diverts the solid waste in a second direction 695B away from the solid body access, the second direction 695B being different than the first direction 695A. Additionally, the solid waste can contact the interior side of the solid receiver guide 667A which guides the solid waste in a third direction 695C toward the solid body access 621BA, the third direction 695C being different than the first direction 695A and the second direction 695B. In one embodiment, the solid waste can be guided away from the solid body access 621BA by the solid waste diverters 658 prior to the solid receiver guide 667A guiding the solid waste toward the solid body access 621BA. Further, in certain alternative embodiments, the solid receiver guide 667A can include greater than or less than two solid waste diverters 658, and/or the solid waste can be guided and/or diverted in more than two directions 695A, 695B prior to being guided, e.g., in the third direction 695C, toward the solid body access 621BA.

Additionally, it should be noted that the use of the terms "first direction", "second direction", and "third direction" is merely for ease of description and any of the directions can be described as the first, second and/or third directions, provided at least two of the directions are different from one another.

In one embodiment, the solid receiver guide 667A includes a guide flap 689 at or near the bottom of the solid receiver guide 667A, i.e. near the solid body access 621BA. In one such embodiment, the guide flap 689 is hinged so that the guide flap 689 can move between an open position and a closed position as indicated by arrow 690. In FIG. 8A, the guide flap 689 is shown in the open position. In one embodiment, the guide flap 689 can include a flap weight 691 that maintains the guide flap 689 in the open position when the solid waste receiver 614 is in an upright position, such as that illustrated in FIG. 8A. In the event the solid waste receiver 614 is moved to an inverted position, the flap weight 691 will cause the guide flap 689 to move to the closed position so that solid waste will be inhibited from exiting the solid receiver body 621. The solid receiver guide 667A can also include a flap stop 692 that inhibits movement of the guide flap 689 beyond the open position illustrated in FIG. 8A.

The fluid absorber 670 can be included inside the solid receiver body 621 to absorb any fluid waste that may inadvertently be deposited into the solid receiver body 621 and/or that may be a by-product of the breakdown of any solid waste.

The reaction agent 687 can react with water or other fluids in order to chemically and/or physically break down any solid waste inside the solid receiver body 621, and/or make the solid waste undesirable and/or indigestible, once the solid receiver body 621 is determined to be ready for capping (i.e. at or near capacity, or at or near expiration). Stated another way, prior to capping the solid receiver body 621, a liquid is added to the solid receiver body 621, which catalyzes a reaction with the reaction agent 687 to destroy or otherwise chemically and/or physically change the solid waste to an unusable and/or unrecoverable form. Alternatively, a liquid is added that solidifies the reaction agent 687 to encapsulate or otherwise surround the solid waste in the solid receiver body 621. The solid receiver body 621 can then be capped, and is then ready for permanent disposal.

In one embodiment, the adherer 688 is positioned at least along a portion of the inside of the solid receiver body 621. The adherer 688 can be an adhesive material or any other suitable material that promotes adherence of the solid waste to the inside of the solid receiver body 621. The adherer 688 adds another layer of protection to inhibit solid waste from being removed from the solid receiver body 621.

It should be noted that although FIG. 8A illustrates and describes an embodiment of the solid receiver guide 667A, the particular features of this solid receiver guide 667A can be equally applicable for one or more of the waste guides 44A, 44B (illustrated in FIG. 1A) and the fluid receiver guide 62 (illustrated in FIG. 1C) as described above.

FIG. 8B is an alternative cross-sectional view of a portion of the solid waste receiver 614 taken on line 8-8 in FIG. 6, with the solid receiver cap 620 (illustrated in FIG. 6) removed for clarity. The solid waste receiver 614 illustrated in FIG. 8B is substantially similar to the solid waste receiver 614 illustrated in FIG. 8A, with the exception of the particular design of the solid receiver guide 667B.

In this embodiment, the solid receiver guide 667B includes a spiral funnel 696 that guides the solid waste in a plurality of directions away from and toward the solid body access 621BA of the solid receiver body 621. In particular, because the spiral funnel 696 has a generally curved shape, the solid waste can be continuously guided and/or redirected in a plurality of different directions away from the solid body access 621BA in addition to the solid waste being guided by the solid receiver guide 667B toward the solid body access 621BA. By way of illustration, the solid waste can be guided and/or redirected by the spiral funnel 696 in a first direction 697A, a second direction 697B, and a third direction 697C away from the solid body access 621BA, in addition to being guided and/or redirected by the solid receiver guide 667B in a fourth direction 697D toward the solid body access 621BA. In one embodiment, the solid waste can be guided and/or redirected away from the solid body access 621BA by the spiral funnel 696 prior to the solid receiver guide 667B guiding and/or redirecting the solid waste toward the solid body access 621BA. Additionally and/or alternatively, due to the continuous curve of the spiral funnel 696, the solid waste can be described as being guided and/or redirected by the spiral funnel 696 in greater than three directions in addition to being guided and/or redirected by the solid receiver guide 667B toward the solid body access 621BA.

Additionally, it should be noted that the use of the terms "first direction", "second direction", "third direction", and "fourth direction" is merely for ease of description and any of the directions can be described as the first, second, third and/or fourth directions, provided at least two of the directions are different from one another.

Further, it should be noted that although FIG. 8B illustrates and describes an embodiment of the solid receiver guide 667B, the particular features of this solid receiver guide 667B can be equally applicable for one or more of the waste guides 44A, 44B (illustrated in FIG. 1A) and the fluid receiver guide 62 (illustrated in FIG. 1C) as described above.

Figure 9:
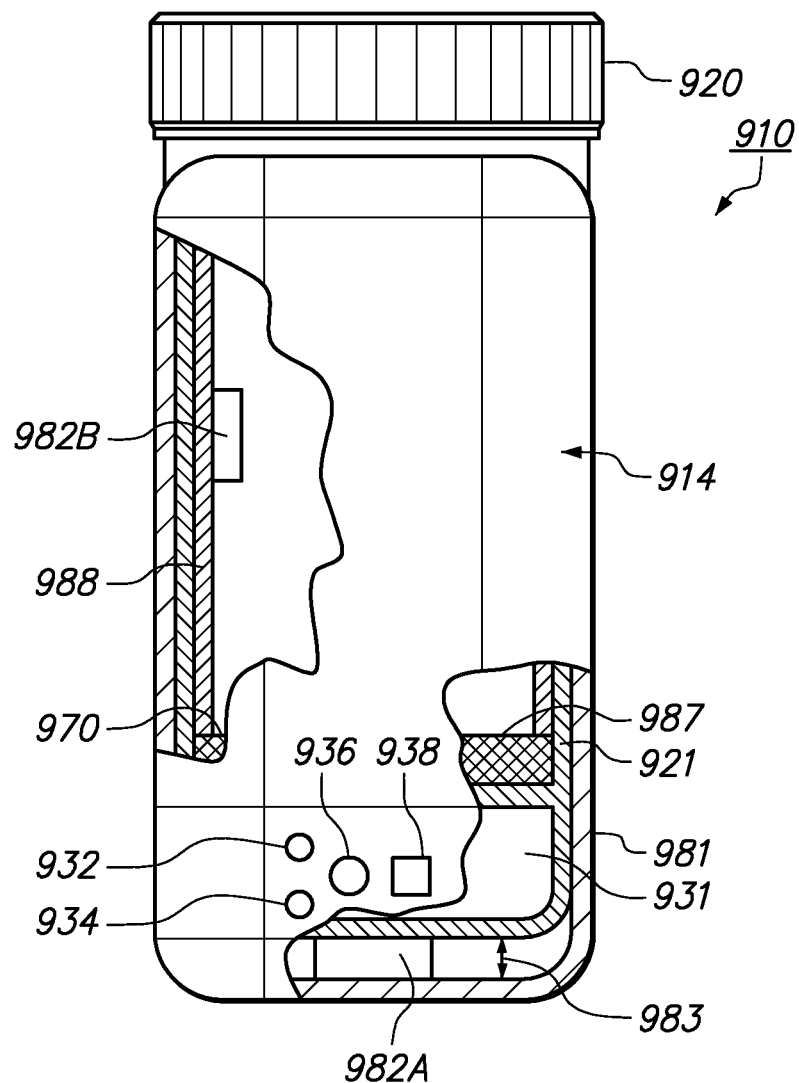
FIG. 9 is a partial cutaway view of yet another embodiment of the pharmaceutical waste disposal assembly.

FIG. 9 is a partial cutaway view of yet another embodiment of the disposal assembly 910. FIG. 9 is a partial cutaway view of another embodiment of a disposal assembly 910 including a solid waste receiver 914. In this embodiment, the solid waste receiver 914 is fully self-contained and is not used in conjunction with a separate receiver retainer (such as receiver retainer 16 illustrated in FIG. 1A). Although not necessarily illustrated in FIG. 9, the solid waste receiver 914 can include the same components illustrated and described relative to FIGS. 6 and 8, including the solid receiver guide 667, which functions substantially as described previously herein.

Additionally, in the embodiment illustrated in FIG. 9, the disposal assembly 910 includes a solid receiver cap 920, a solid receiver body 921, a controller 931, a charged battery indicator 932, a low battery indicator 934, a solid waste receiver indicator 936, a fluid absorber 970, a reaction agent 987 and an adherer 988, which function substantially as previously described herein, with the exception of certain modifications provided below. Further, the disposal assembly 910 can also include a timer activator 938, a solid receiver body retainer 981 and one or more solid waste receiver sensors 982A, 982B.

In one embodiment, the solid receiver body 921 is positioned within and is movable relative to the solid receiver body retainer 981 in a direction illustrated by arrow 983. Movement of the solid receiver body 921 relative to the solid receiver body retainer 981 only needs to be slight, and is dependent upon the weight of the contents of the solid receiver body 921, including any solid waste which may be present within the solid receiver body 921. In the embodiment illustrated in FIG. 9, a solid waste receiver sensor 982A is positioned between the solid receiver body 921 and the solid receiver body retainer 981. In one embodiment, the solid waste receiver sensor 982A is a weight sensor, such as a load cell, for example. In this embodiment, as the weight of the solid receiver body 921 and its contents increases, a greater force is exerted on the weight sensor 982A.

In one embodiment, the weight sensor 982A can convert a predetermined force into an electrical signal, which causes the solid waste receiver indicator 936 to activate. Activation of the solid waste receiver indicator 936 can alert a user that the solid waste has reached a predetermined percentage of the capacity of the solid receiver body 921, and the user has a certain predetermined time period to place the solid receiver cap 920 on the solid receiver body 921, which prepares the disposal assembly 910 for disposal. In various embodiments, the predetermined force required to activate the solid waste receiver indicator 936 and/or the predetermined percentage of the capacity of the solid receiver body 921 can be determined based upon various requirements of the specific regulations governing disposal of waste. Alternatively, the predetermined force required to activate the solid waste receiver indicator 936 and/or the predetermined percentage of the capacity of the solid receiver body 921 can be determined by the user, and can be programmed into the controller 931.

In another embodiment, the solid waste receiver indicator 936 can be activated by the solid waste receiver sensor 982B. In this embodiment, as the level of solid waste rises in the solid receiver body 921, the solid waste generates a force against the solid waste receiver sensor 982B. Once a predetermined force has been achieved, the solid waste receiver sensor 982B transmits an electrical signal to the controller 931. The controller 931 then activates the solid waste receiver indicator 936 to alert a user that the solid waste has reached a predetermined percentage of the capacity of the solid receiver body 921. At this point, in one embodiment, the user has a certain predetermined time period to place the solid receiver cap 920 on the solid receiver body 921, which prepares the disposal assembly 910 for permanent disposal.

In this embodiment, the specific type of solid waste receiver sensor 982B can vary. In one embodiment, the solid waste receiver sensor 982B can be a load cell. Alternatively, the solid waste receiver sensor 982B can include one or more piezoelectric elements. Still alternatively, other types of sensors can be used that can transmit an electrical signal based on mechanical movement of the solid waste receiver sensor 982B caused by pressure or force exerted by the rising level of solid waste in the solid receiver body 921.

In certain embodiments, the timer activator 938 can manually be activated by the user once usage of the disposal assembly 910 has commenced. In one embodiment, the timer activator 938 notifies the controller 931 to start a clock or other timekeeping device. Once a predetermined period of time has elapsed, the controller 931 can activate the solid waste receiver indicator 936, which alerts the user that a specific time period has passed, and that the useful life of the disposal assembly 910 has either expired, or that expiration is imminent or within a predetermined time period of expiration. For example, if expiration of the disposal assembly 910 occurs at 90 days from activation of the timer activator, the controller 931 may activate the solid waste receiver indicator 936 at 75 days to provide a 15-day lead time for the user to terminate usage of the disposal assembly 910. It is understood that the foregoing example is provided for ease of understanding only, and is not intended to limit in any manner the time periods for which the invention may be used.

Figure 10:
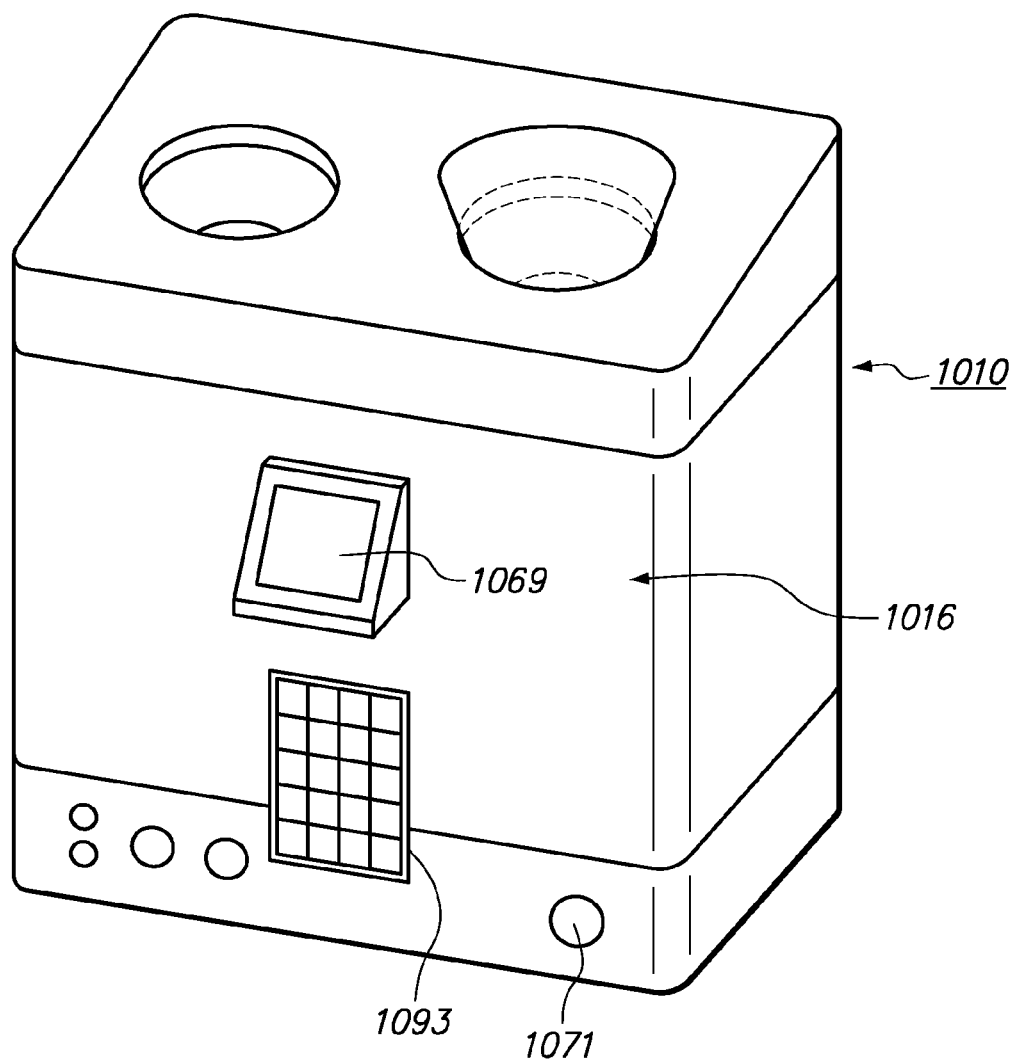
FIG. 10 is a front perspective view of one embodiment of the receiver retainer.

FIG. 10 is a front perspective view of one embodiment of a disposal assembly 1010, including a receiver retainer 1016. Although not necessarily illustrated in FIG. 10, the disposal assembly 1010 can include some or all of the same features illustrated and described previously herein. In the embodiment illustrated in FIG. 10, the receiver retainer 1016 includes an input device 1093, such as a keypad or a touchscreen as non-exclusive examples. The input device 1093 is utilized by a user to input certain relevant information, such as drug classification (as one non-exclusive example), that can be communicated to the controller 31 (illustrated in FIG. 1C, for example) for further processing. Additionally, or alternatively, the input device 1093 can be used to identify and/or authenticate a user for access to the disposal assembly 1010. In one embodiment, the user can type a passcode or other authentication information into the input device 1093. Alternatively, other types of authentication methods can be included, such as a badge scanner or barcode reader, as non-exclusive alternative examples. The design of the input device 1093 can be varied to suit the design requirements of the disposal assembly 1010. In one embodiment, the input device 1093 can receive, store and/or transmit, information regarding the type of waste that is being deposited into the disposal assembly 1010.

Additionally, or in the alternative, the disposal assembly 1010 can include an output device 1069 that can display certain relevant information to the user. By way of example and not by way of limitation, the output device 1069 can display information such as current fill level(s) of the waste receivers, expiration dates of the waste receivers, time remaining prior to expiration, the types of waste that have previously been deposited into the waste receivers, user input information, drug classifications, remaining battery life, alert information, and any other relevant information that could possibly be utilized by a user of the disposal assembly 1010.

In the embodiment illustrated in FIG. 10, the disposal assembly 1010 also includes a monitoring device 1071. In this embodiment, the monitoring device 1071 can include a video and/or audio recorder, such as a video camera or a sound recorder, as non-exclusive examples. The monitoring device 1071 can be utilized to monitor and/or record video and/or audio of the usage of the disposal assembly 1010 by the user(s). A real-time and/or previously recorded video and/or audio feed can be stored in the disposal assembly 1010, such as in a memory of the controller (not illustrated in FIG. 10), for example, or in some other location within the disposal assembly 1010. Alternatively, the video and/or audio feed can be transmitted to another location not within the disposal assembly, such as a separate monitor or screen (not shown), a video recording device (not shown), or any other suitable location for storage and/or viewing of the recorded video data.

Figure 11A:
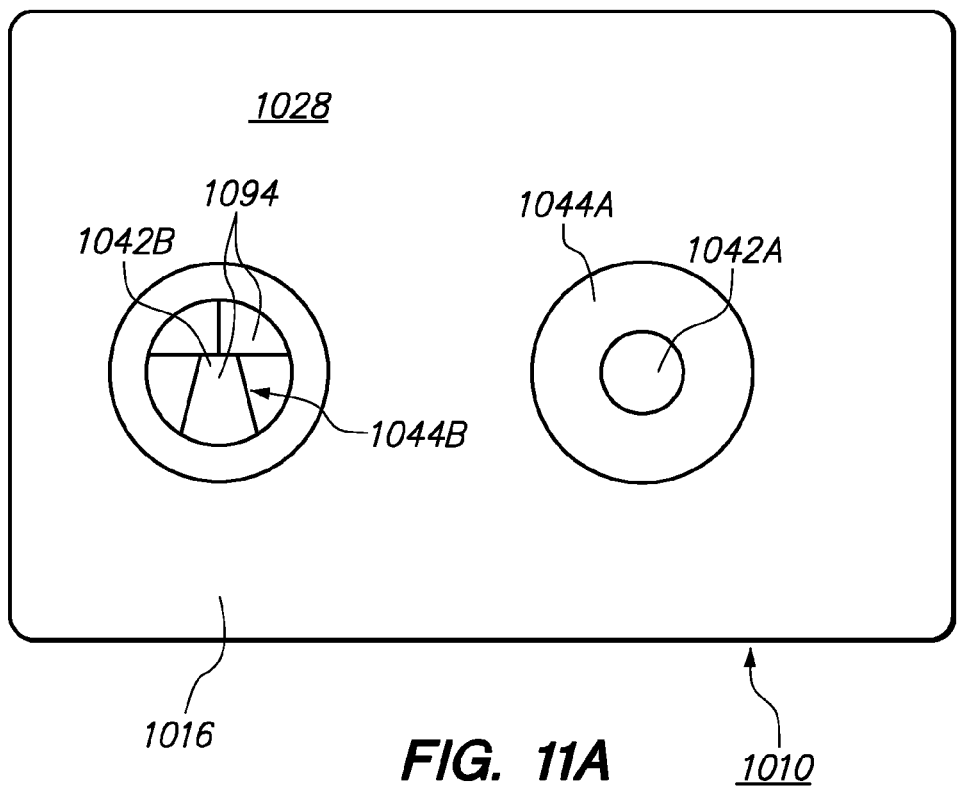
FIG. 11A is a simplified top view of the pharmaceutical waste disposal assembly, including the receiver retainer shown in FIG. 10, illustrated in the closed position.

FIG. 11A is a simplified top view of the disposal assembly 1010, including the receiver retainer 1016 illustrated in FIG. 10, with the input device 1093 omitted. In this embodiment, the receiver retainer 1016 is shown in the closed position. In one embodiment, the receiver retainer 1016 includes a retainer lid 1028 having one or more lid apertures (a fluid lid aperture 1042A and a solid lid aperture 1042B are illustrated in FIG. 11A). The lid apertures 1042A, 1042B function substantially in the same manner as those previously described herein, allowing fluid waste and/or solid waste to be deposited into one of the waste receivers (not shown in FIG. 11A) from outside of the receiver retainer 1016. In this embodiment, the lid apertures 1042A, 1042B are positioned in, and extend through, the retainer lid 1028.

In the embodiment illustrated in FIG. 11A, the fluid lid aperture 1042A includes a fluid waste guide 1044A, and the solid lid aperture 1042B includes a solid waste guide 1044B. Each waste guide 1044A, 1044B assists in directing the specific phase of waste (solid, liquid or gas) to the appropriate waste receiver. In this embodiment, the fluid waste guide 1044A includes a funnel-type device. Further, the solid waste guide 1044B includes a funnel-type device in combination with one or more diverters 1094 that guide or otherwise direct the waste to the appropriate waste receiver, in a manner substantially similar or identical to that previously described herein. It is understood that either of the lid apertures 1042A, 1042B can include any type of waste guide 1044A, 1044B, and that the specific combinations of lid apertures 1042A, 1042B and waste guides 1044A, 1044B illustrated in FIG. 11A are provided for ease of understanding only, and are not intended to be limiting in any manner.

Figure 11B:
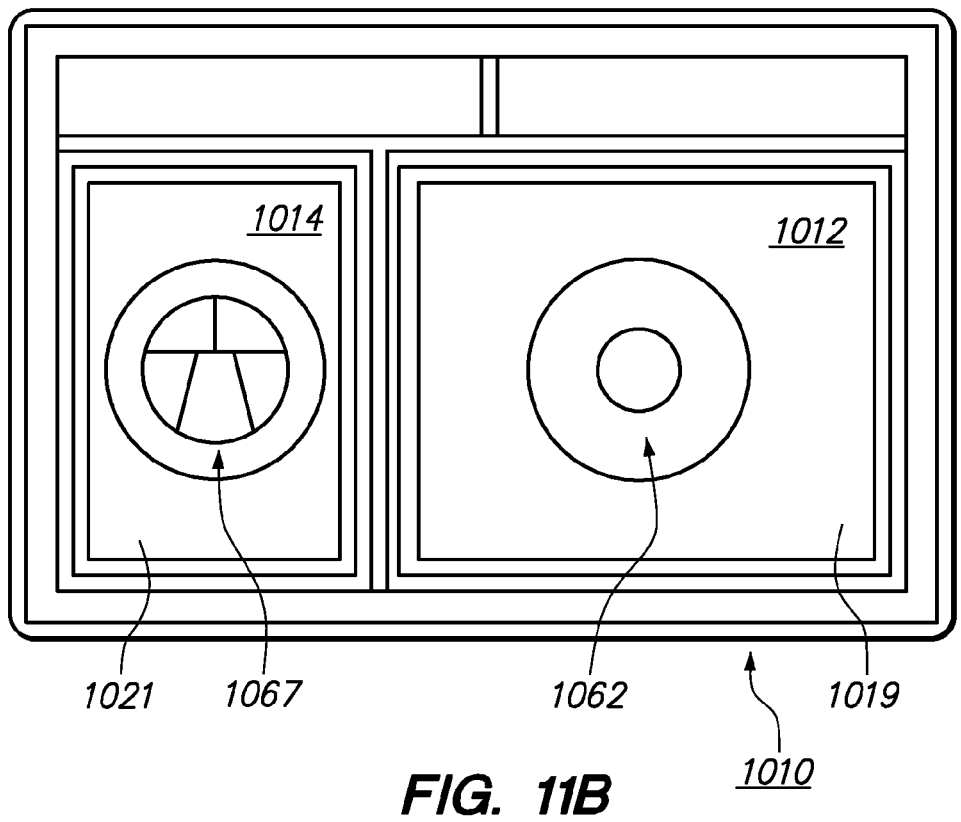
FIG. 11B is a simplified top view of a portion of one embodiment of the pharmaceutical waste disposal assembly illustrated in FIG. 10, illustrated in the open position.

FIG. 11B is a simplified top view of a portion of the disposal assembly 1010 illustrated in FIG. 10, illustrated in the open position, with the retainer lid 1028 and the input device 1093 removed for clarity. In this embodiment, the disposal assembly 1010 includes the fluid waste receiver 1012 and the solid waste receiver 1014. The fluid waste receiver 1012 includes a fluid receiver guide 1062 that guides the fluid waste into the fluid receiver body 1019. The fluid receiver guide 1062 can include a standard funnel-type device (as illustrated in FIG. 11B) a spiral funnel, or a series of diverters.

In this embodiment, the solid waste receiver 1014 includes a solid receiver guide 1067 that guides the solid waste into the solid receiver body 1021. The solid receiver guide 1067 can include a standard funnel-type device, a spiral funnel, or a series of diverters (as illustrated in FIG. 11B).

When the disposal assembly 1010 illustrated in FIG. 11B is combined with the retainer lid 1028 illustrated in FIG. 11A, both a corresponding waste guide 1044A, 1044B and a corresponding receiver guide 1062, 1067 serve to guide the specific phase of waste into the appropriate receiver body 1019, 1021. With this design, the likelihood of improper removal of waste from the receiver bodies 1019, 1021 is decreased.

Figure 12:
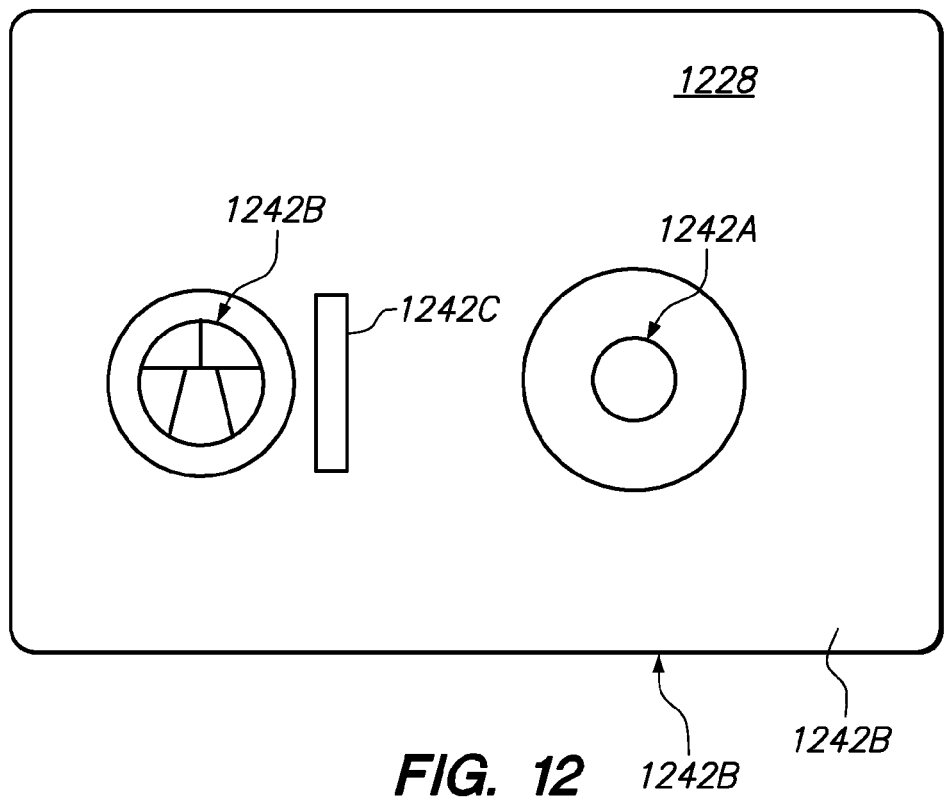
FIG. 12 is a simplified top view of another embodiment of the pharmaceutical waste disposal assembly including the receiver retainer, illustrated in the closed position.

FIG. 12 is a simplified top view of another embodiment of the disposal assembly 1210 including the receiver retainer 1216, illustrated in the closed position. In this embodiment, the receiver retainer 1216 includes a retainer lid 1228 that is substantially similar to the retainer lid 1028 illustrated and described relative to FIG. 11A, with certain noted exceptions.

In the embodiment illustrated in FIG. 12, in addition to a fluid lid aperture 1242A, the receiver retainer 1216 also includes a first solid lid aperture 1242B and a second solid lid aperture 1242C. The first solid lid aperture 1242B is substantially similar to the solid lid aperture 1042B illustrated and described relative to FIG. 11A.

The second solid lid aperture 1242C is designed to receive solid waste in the form of pharmaceutical and/or medical patches and the like. The size and configuration of the second solid lid aperture 1242C can vary. In one embodiment, the second solid lid aperture 1242C can have a somewhat rectangular, slot-like configuration. Alternatively, the second solid lid aperture 1242C can have another suitable configuration that is consistent with accepting pharmaceutical and/or medical patches. The solid waste that is deposited into the second solid lid aperture 1242C can be received by the same solid waste receiver (not illustrated in FIG. 12) that receives solid waste via the first solid lid aperture 1242B. Alternatively, the solid waste that is deposited into the second solid lid aperture 1242C can be received by a different solid waste receiver than the solid waste receiver that receives solid waste via the first solid lid aperture 1242B.

Figure 13:
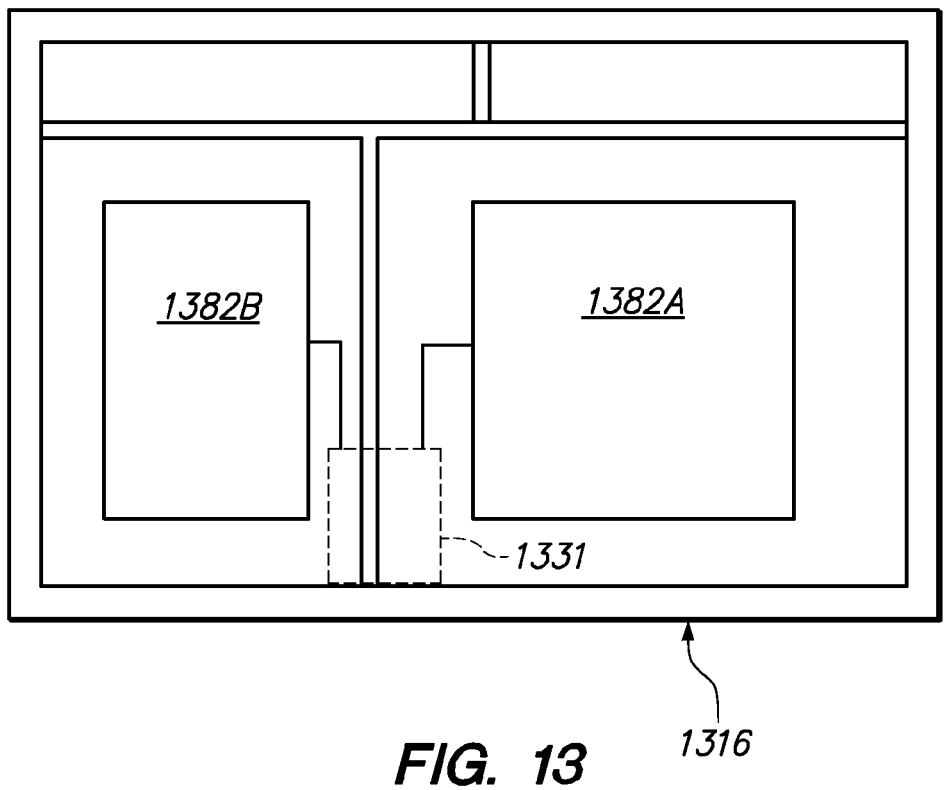
FIG. 13 is a simplified top view of one embodiment of a portion of the receiver retainer, illustrated in the open position.

FIG. 13 is a simplified top view of one embodiment of a portion of a receiver retainer 1316, illustrated in the open position, with the retainer lid omitted for clarity. In this embodiment, the receiver retainer 1316 includes a controller 1331 (illustrated in phantom), a fluid waste receiver sensor 1382A and a solid waste receiver sensor 1382B. In one embodiment, the waste receiver sensors 1382A, 1382B are weight sensors, such as a load cell, for example, and function in a substantially similar or identical manner as those previously described herein. In this embodiment, once the weight of the contents of one or both of the receiver bodies (not shown in FIG. 13) increases to a predetermined level, the weight sensor 1382A, 1382B will send an electrical signal to the controller 1331, which can then activate the appropriate waste receiver indicator 36, 38 (illustrated in FIG. 1A, for example), as necessary.

Figure 14:
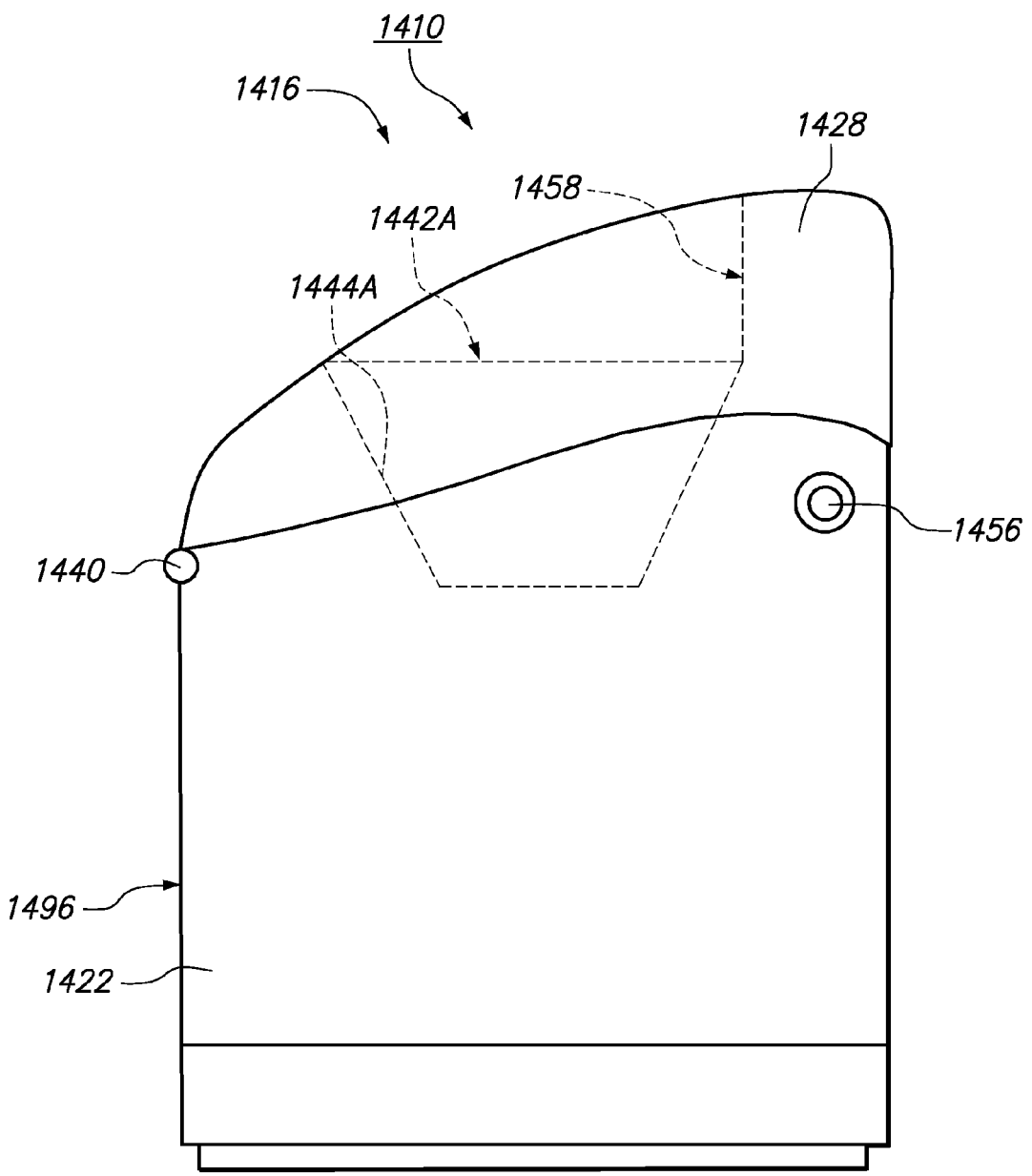
FIG. 14 is a side elevation of another embodiment of the receiver retainer.

FIG. 14 is a side elevation of another embodiment of a receiver retainer 1416. In this embodiment, the configuration of the retainer lid 1428 is such that a fluid waste diverter 1458 (illustrated in phantom) is built directly into the retainer lid 1428 so that a separate fluid waste diverter is unnecessary. The fluid waste diverter 1458 diverts and/or directs fluid waste to the fluid lid aperture 1442A (illustrated in phantom) and the fluid waste guide 1444A (illustrated in phantom).

Additionally, in this embodiment, the retainer lid 1428 is movably secured to the retainer housing 1422 by one or more hinges 1440. In this embodiment, the one or more hinges 1440 are secured to a retainer front 1496 so that in the event the disposal assembly 1410 is backed up against a wall or other surface, opening of the retainer lid 1428 will not be impeded.

In the embodiment illustrated in FIG. 14, the receiver retainer 1416 also includes a locking mechanism 1456 for locking the retainer lid 1428 in a closed position, as illustrated in FIG. 14. The locking mechanism 1456 can include any suitable type of locking mechanism known to those skilled in the art, including but not limited to a combination lock or a lock requiring one or more of a key, passcode, fingerprint reader, voice recognition, or any other suitable type of lock.

Figure 15:
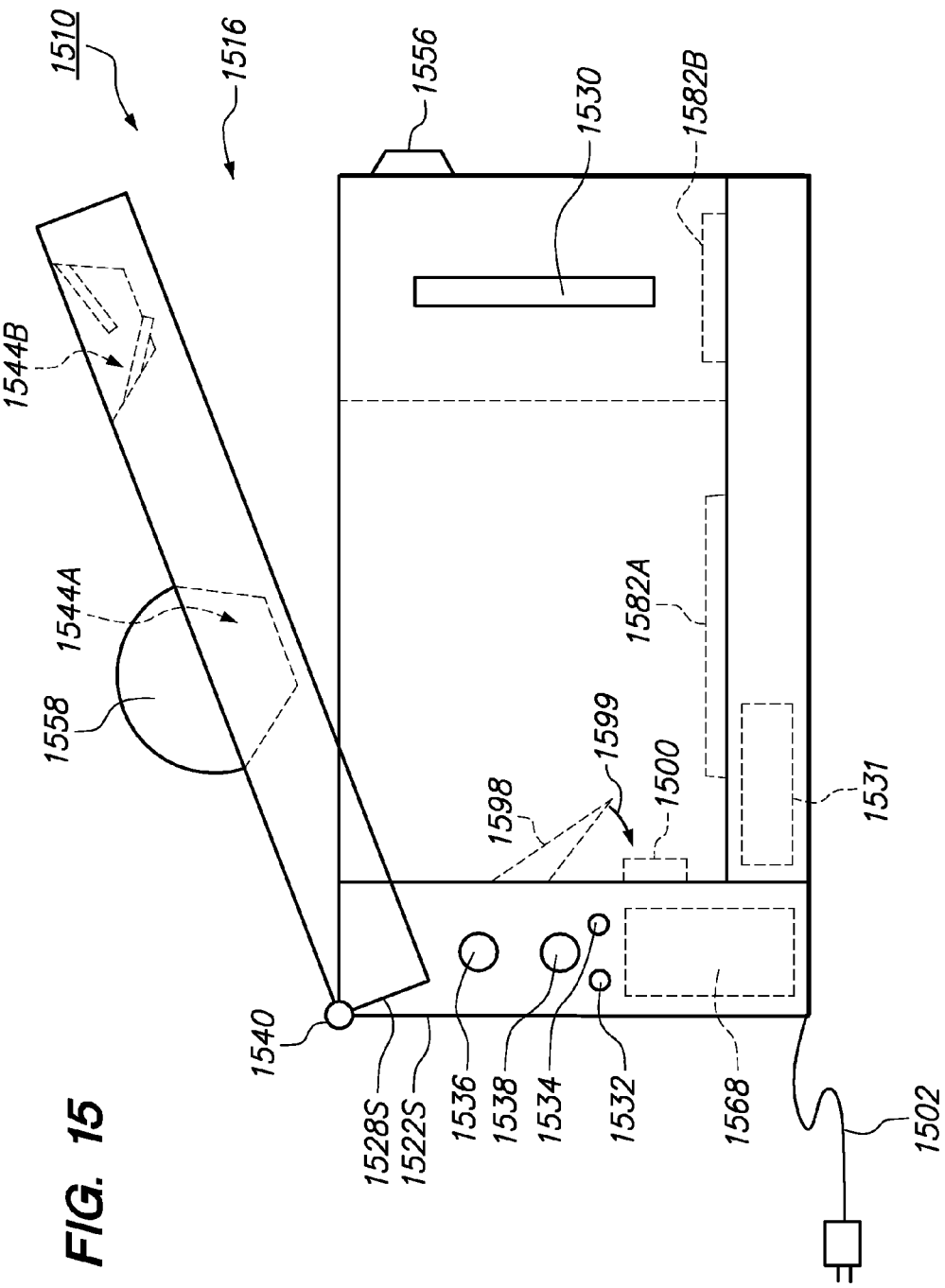
FIG. 15 is a front elevation of yet another embodiment of the receiver retainer, with various internal components illustrated in phantom.

FIG. 15 is a front elevation of yet another embodiment of a receiver retainer 1516, illustrated in an open position. The receiver retainer 1516 can include various features previously described herein, although not specifically illustrated in FIG. 15. Additionally, the receiver retainer 1516 can include one or more viewing windows 1530, a controller 1531, a charged battery indicator 1532, a low battery indicator 1534, a fluid waste receiver indicator 1536, a solid waste receiver indicator 1538, one or more hinges 1540, a fluid waste guide 1544A, a solid waste guide 1544B, a locking mechanism 1556, a fluid waste diverter 1558, an electrochemical cell structure 1568, and one or more waste receiver sensors 1582A, 1582B, each of which function substantially as previously described herein, with the exception of certain modifications noted herein. Further, the receiver retainer 1516 can also include a timer activator 1598, an identification reader 1500, and an AC power supply cord 1502.

In this embodiment, the hinges 1540 are secured to a housing side panel 1522S and a lid side panel 1528S so that the retainer lid 1528 opens to one side, as illustrated in FIG. 15. With this design, the retainer lid 1528 of the receiver retainer 1516 will not be impeded and can still be opened even when the receiver retainer 1516 is backed against a wall or is mounted to a wall, for example.

In one embodiment, at any time that the retainer lid 1528 is in the open position, an audible and/or visual indicator or alert is activated. With this design, users can be notified in the event of unauthorized (or authorized) access to the interior of the receiver retainer 1516 occurs.

In the embodiment illustrated in FIG. 15, the timer activator 1598 operates substantially similarly to the timer activator 538 illustrated in FIG. 5, except the timer activator 1598 in FIG. 15 is automatically activated when a waste receiver (not shown in FIG. 15) is initially placed into the receiver retainer 1516. In one embodiment, the timer activator 1598 is moved by the waste receiver in a direction as indicated by arrow 1599 when the waste receiver is placed into the receiver retainer 1516. When the timer activator 1598 is activated, the timer activator 1598 notifies the controller 1531 to start a clock or other timekeeping device. Once a predetermined period of time has elapsed, the controller 1531 can activate the fluid waste receiver indicator 1536, which alerts the user that a specific time period has passed, and that the useful life of the disposal assembly 1510 has either expired, or that expiration is imminent or within a predetermined time period of expiration.

The identification reader 1500 can detect and/or read an identification tag 200 (illustrated in FIG. 2, for example) positioned on one or more waste receivers (not shown in FIG. 15). Although only one identification reader 1500 is illustrated in FIG. 15, it is understood that additional identification readers can be positioned in different locations on or within the receiver retainer 1510. For example, the identification reader 1500 illustrated in FIG. 15 is positioned to read an identification tag that is positioned on a fluid waste receiver. However, the identification reader 1500 can equally be positioned in another location for reading an identification tag positioned on a solid waste receiver, for example.

In one embodiment, the identification reader 1500 can read an RFID tag, an integrated circuit, a barcode label, or any other suitable type of identifying tag that is included in either or both the fluid waste receiver and the solid waste receiver (not shown in FIG. 15). The identification reader 1500 can serve one or more purposes. In one embodiment, the identification reader 1500 can transmit a signal to the controller 1531 to activate a clock or other timer once the fluid waste receiver and/or solid waste receiver are properly positioned within the receiver retainer 1516. As provided hereinabove, the timer can be used to determine when the waste receiver is expired or will soon expire as of a predetermined number of hours, days, etc. from the time the clock is activated. Data from the identification reader 1500 can be transmitted to and/or stored within the controller 1531.

In another embodiment, the identification reader 1500 can alternatively, or in addition, store information from the identification tag on the waste receiver so that a particular waste receiver cannot be used twice. For example, the identification reader 1500 can read unique information from a specific identification tag, and store this information in the controller 1531 or in memory outside of the receiver retainer 1516. Once the waste receiver is removed from the receiver retainer 1516, if the same waste receiver is ever placed back into the receiver retainer 1516, the identification reader 1500, in conjunction with the controller 1531, will recognize the waste receiver as being the same waste receiver that was previously utilized with the receiver retainer 1516. In one embodiment, the appropriate receiver indicator 1536, 1538 will be activated to alert a user of the reuse of the waste receiver.

In another embodiment, the identification reader 1500 can alternatively, or in addition, store information from the identification tag on the waste receiver in a centralized database that can be accessed by others to track location, shipment or delivery of the waste receiver to a permanent disposal site, to locations within a hospital or other health care facility, or another suitable locations.

The AC power supply cord 1502 can be used to transmit AC power to the disposal assembly 1510 to charge the electrochemical cell structure 1568, or to power the entire disposal assembly 1510 in embodiments that do not include a electrochemical cell structure 1568, or in the event the electrochemical cell structure 1568 is low or dead.

Figure 16:
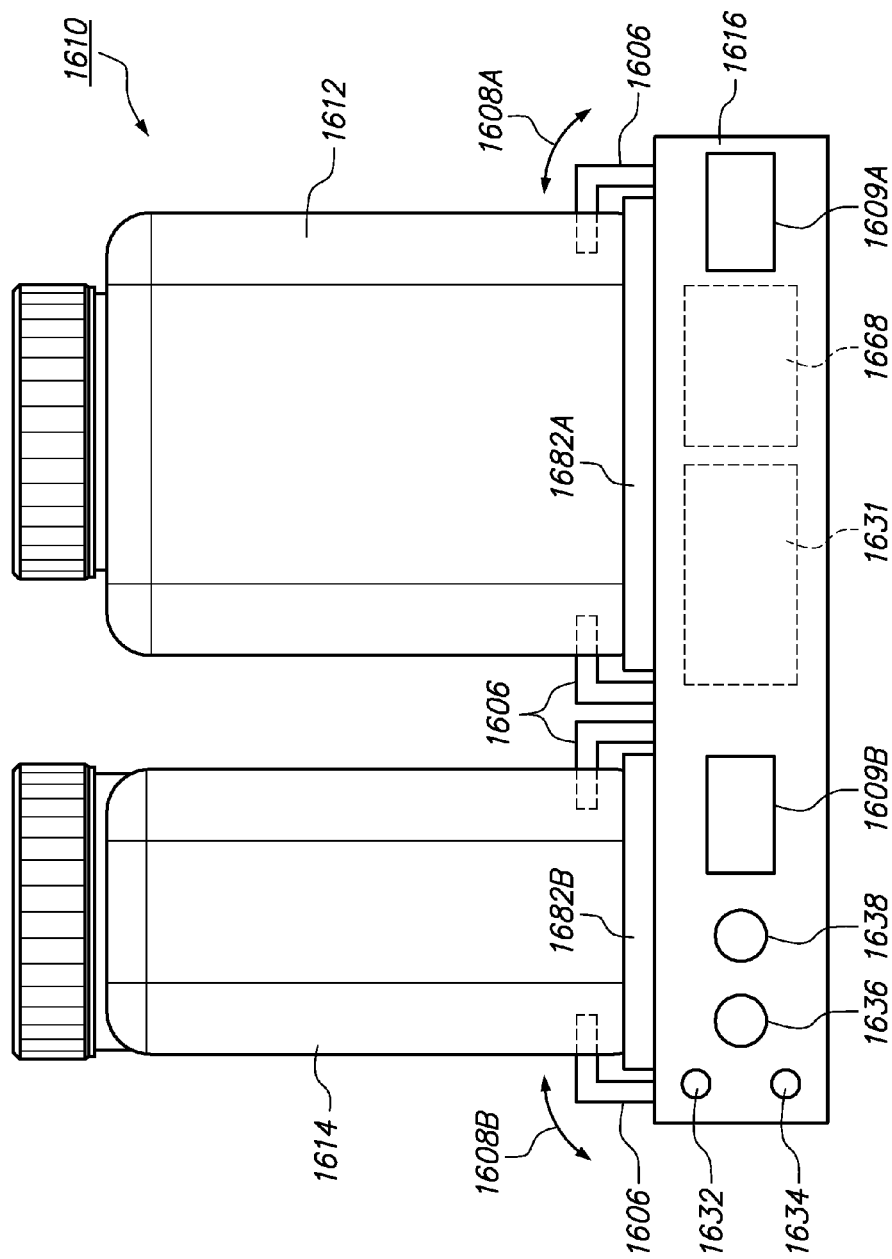
FIG. 16 is a front elevation of yet another embodiment of a pharmaceutical waste disposal assembly having features of the present invention.

FIG. 16 is a front elevation of yet another embodiment of a disposal assembly 1610. In this embodiment, the disposal assembly 1610 includes one or both of a fluid waste receiver 1612 and a solid waste receiver 1614. Further, the disposal assembly 1610 includes a receiver retainer 1616. In this embodiment, the receiver retainer 1616 has a platform configuration. The receiver retainer 1616 can include various features previously described herein, although not specifically illustrated in FIG. 16. Additionally, the receiver retainer 1616 can include a controller 1631 (illustrated in phantom), a charged battery indicator 1632, a low battery indicator 1634, a fluid waste receiver indicator 1636, a solid waste receiver indicator 1638, an electrochemical cell structure 1668, and one or more waste receiver sensors 1682A, 1682B, each of which function substantially as previously described herein, with the exception of certain modifications noted herein. Further, the receiver retainer 1616 can also include one or more receiver securers 1606 (shown partially in phantom where inserted into waste receivers 1612, 1614), a fluid digital readout 1609A and/or a solid digital readout 1609B.

The waste receivers 1612, 1614 are positioned on the receiver retainer 1616, and are held in place by the receiver securers 1606. The receiver securers 1606 can be movably positioned to secure the waste receivers 1612, 1614 to the receiver retainer 1616. In one embodiment, the receiver securers 1606 can be manually moved into place to secure the waste receivers 1612, 1614 to the receiver retainer 1616. Alternatively, the receiver securers 1606 can automatically move into place to secure the waste receivers 1612, 1614 to the receiver retainer 1616. In one such embodiment, the receiver securers 1606 can electromechanically move toward and/or away from the waste receivers 1612, 1614 in the direction of arrows 1608A, 1608B. In an alternative embodiment, the receiver securers 1606 can move toward and/or away from the waste receivers 1612, 1614 by another suitable means.

The digital readouts 1609A, 1609B can provide specific information regarding the status of the waste receivers 1612, 1614. For example, in certain embodiments, the digital readouts 1609A, 1609B can indicate one or more of the length of time the waste receivers 1612, 1614 have been positioned on the receiver retainer 1616, the weight of the waste receivers 1612, 1614, the weight of the contents of the waste receivers 1612, 1614, the expiration date for each of the waste receivers 1612, 1614 based on when they were positioned on the receiver retainer 1616, or any other useful information depending upon the design requirements of the disposal assembly 1610.

Figure 17A:
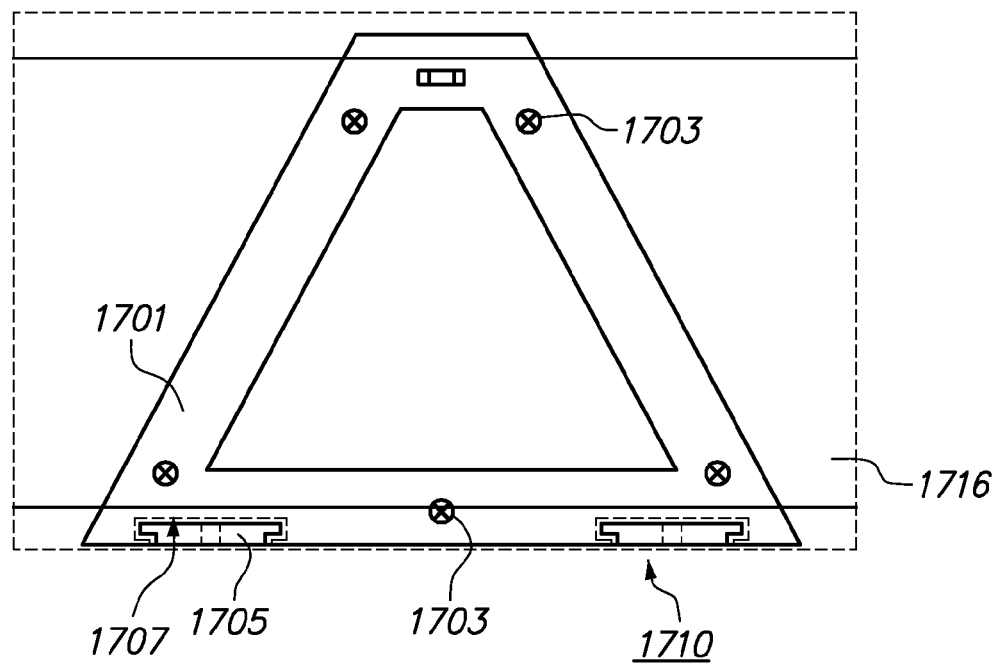
FIG. 17A is a front view of one embodiment of the pharmaceutical waste disposal assembly including a mounting apparatus, and a simplified representation of the receiver retainer (illustrated in phantom) engaged with the mounting apparatus.

FIG. 17A is a front view of one embodiment of the disposal assembly 1710 including a mounting apparatus 1701, and a simplified representation of the receiver retainer 1716 (illustrated in phantom) engaged with the mounting apparatus 1701. In this embodiment, the mounting apparatus 1701 can be secured to a vertical or non-vertical surface with one or more fasteners 1703, such as screws, nails, etc. The specific configuration of the mounting apparatus 1701 can vary. In one embodiment, the mounting apparatus 1701 can have a somewhat triangular configuration. However, in alternative embodiments, the mounting apparatus 1701 can have a square, curved, circular, elliptical, polygonal or another suitable configuration.

In this embodiment, the mounting apparatus 1701 includes one or more support rails 1705 (two support rails are illustrated in FIG. 17A) that support the receiver retainer 1716. The support rails 1705 slidingly interlock with corresponding complementary rail receivers 1707 on the receiver retainer 1716. As provided in greater detail herein, the receiver retainer 1716 can slide onto the support rails 1705, and then be lockingly secured to the mounting apparatus 1701 for stability and security.

Figure 17B:
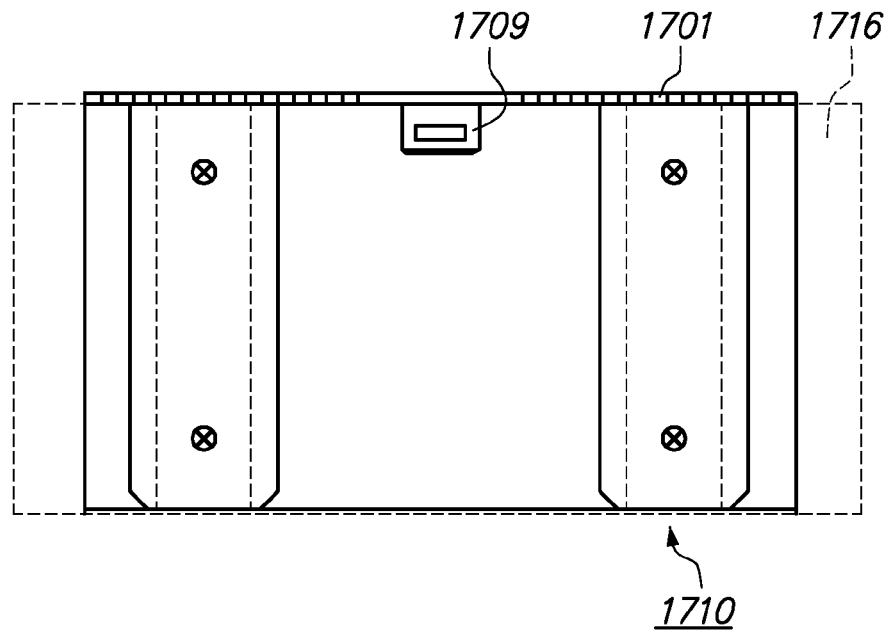
FIG. 17B is a top view of the mounting apparatus illustrated in FIG. 17A.

FIG. 17B is a top view of the disposal assembly 1710 including the mounting apparatus 1701 illustrated in FIG. 17A, and the receiver retainer 1716 illustrated in phantom for differentiation. In this embodiment, the mounting apparatus 1701 includes a locking tab 1709 that extends into the receiver retainer 1716 as provided in greater detail herein.

Figure 17C:
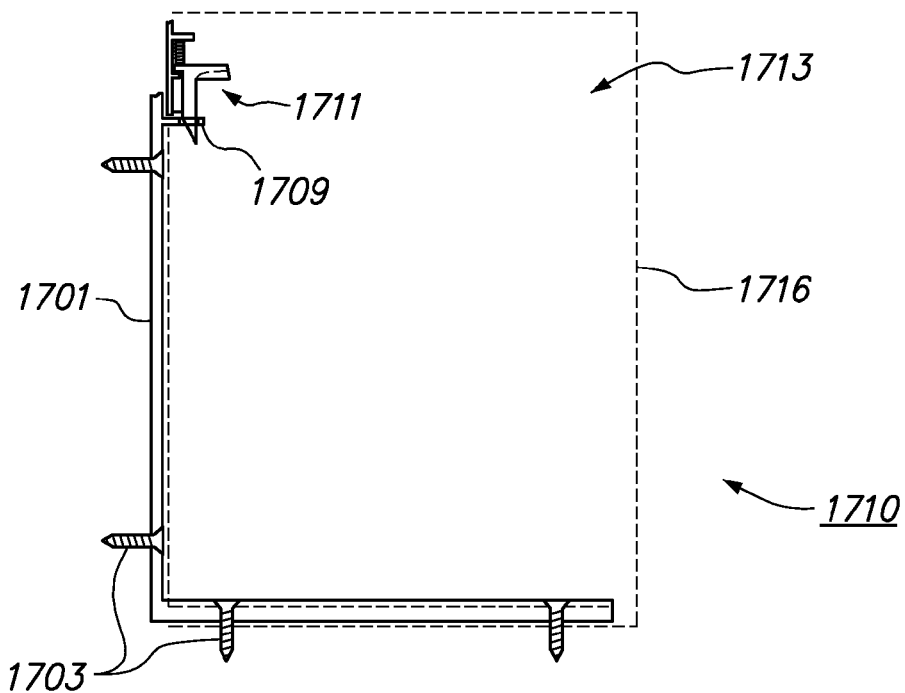
FIG. 17C is a side elevation of the mounting apparatus illustrated in FIG. 17A, and one simplified embodiment of the receiver retainer (illustrated in phantom) engaged with the mounting apparatus.

FIG. 17C is a side elevation of disposal assembly 1710 including the mounting apparatus 1701 illustrated in FIG. 17A, and the receiver retainer 1716 (illustrated in phantom) engaged with the mounting apparatus 1701. In this embodiment, it is evident that the mounting apparatus 1701 can be secured with fasteners 1703 to one or both of two surfaces that are substantially perpendicular to one another. Further, in this embodiment, the receiver retainer 1716 includes a locking pin assembly 1711 that is positioned in a retainer interior 1713 of the receiver retainer 1716. The locking pin assembly 1711 lockingly engages the locking tab 1709 of the mounting apparatus 1701 to secure the receiver retainer 1716 to the mounting apparatus 1701. In certain embodiments of the receiver retainer 1716 that include a locking mechanism (as previously described herein), the locking pin assembly 1711 cannot be unlocked from the locking tab 1709 unless the receiver retainer 1716 can be opened to access the locking pin assembly 1711. With this design, unauthorized persons will be inhibited from disengaging the receiver retainer 1716 from the mounting apparatus 1701.

Figure 17D:
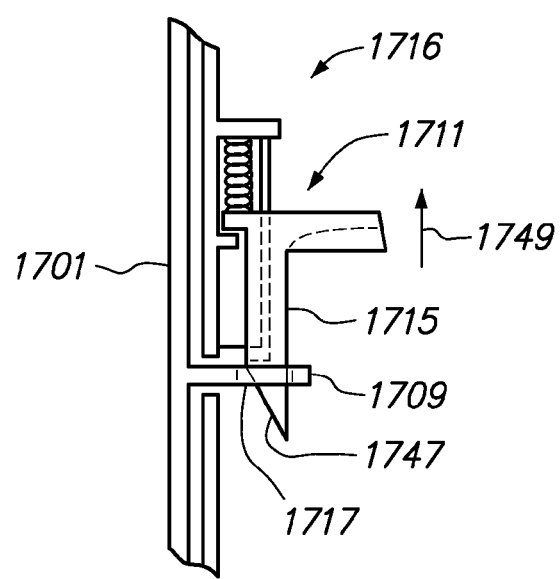
FIG. 17D is a detailed side view of a portion of the mounting apparatus engaged with a portion of the receiver retainer.

FIG. 17D is a detailed side view of a portion of the mounting apparatus 1701 including the locking tab 1709, and a portion of the receiver retainer 1716, including the locking pin assembly 1711, illustrated in an engaged position. In this embodiment, the locking pin assembly 1711 is spring loaded so that a locking pin 1715 is biased to extend through a tab aperture 1717 in the locking tab 1709. The locking pin 1715 can have an angled tip 1747 to allow the locking pin 1715 to enter the tab aperture 1717 without the need to manually lift the locking pin 1715 in an upwardly direction (indicated by arrow 1749). However, to remove the locking pin 1715 from the tab aperture 1717, it is necessary to manually lift the locking pin 1715 in the upwardly direction 1749, which in one embodiment, can only be accomplished from the retainer interior 1713 (illustrated in FIG. 17C).

It is understood that although a number of different embodiments of the pharmaceutical waste disposal assembly 10 have been illustrated and described herein, one or more features of any one embodiment can be combined with one or more features of one or more of the other embodiment, provided that such combination satisfies the intent of the present invention.

While a number of exemplary aspects and embodiments of a pharmaceutical waste disposal assembly 10 have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A pharmaceutical waste disposal assembly for disposing of one or more of fluid pharmaceutical waste and solid pharmaceutical waste, the pharmaceutical waste disposal assembly comprising:
   a first waste receiver including a first receiver body having a first body access, the pharmaceutical waste moving in a first direction that is directly toward the first body access through which the pharmaceutical waste is received by the first receiver body; and
   a receiver retainer that substantially encloses the first waste receiver, the first waste receiver being removable from the receiver retainer;
   wherein one of the first waste receiver and the receiver retainer includes a first waste guide that guides the pharmaceutical waste in a second direction away from the first body access and in the first direction toward the first body access.

2. The pharmaceutical waste disposal assembly of claim 1 wherein the first waste guide includes a spiral funnel that guides the pharmaceutical waste in the second direction away from the first body access prior to guiding the pharmaceutical waste in the first direction toward the first body access.

3. The pharmaceutical waste disposal assembly of claim 1 wherein the first waste guide includes a series of diverters that guides the pharmaceutical waste in the second direction away from the first body access prior to guiding the pharmaceutical waste in the first direction toward the first body access.

4. The pharmaceutical waste disposal assembly of claim 1 wherein the first waste guide guides the pharmaceutical waste in a third direction away from the first body access prior to guiding the pharmaceutical waste in the first direction toward the first body access, the third direction being different than the second direction.

5. The pharmaceutical waste disposal assembly of claim 4 wherein the first waste guide guides the pharmaceutical waste in a fourth direction away from the first body access prior to guiding the pharmaceutical waste in the first direction toward the first body access, the fourth direction being different than the second direction and the third direction.

6. The pharmaceutical waste disposal assembly of claim 1 wherein the first waste receiver is a solid waste receiver including a solid receiver body that receives the solid pharmaceutical waste.

7. The pharmaceutical waste disposal assembly of claim 1 wherein the first waste receiver is a fluid waste receiver including a fluid receiver body that receives the fluid pharmaceutical waste.

8. The pharmaceutical waste disposal assembly of claim 1 further comprising a second waste guide that guides the pharmaceutical waste in a third direction away from the first body access and a fourth direction toward the first body access, the first waste receiver including the first waste guide and the receiver retainer including the second waste guide.

9. The pharmaceutical waste disposal assembly of claim 1 further comprising a second waste receiver including a second receiver body having a second body access, the pharmaceutical waste moving in a third direction toward the second body access through which the pharmaceutical waste is directly received by the second receiver body, the receiver retainer substantially enclosing the second waste receiver, wherein one of the second waste receiver and the receiver retainer includes a second waste guide that guides the pharmaceutical waste in a fourth direction away from the second body access and in the third direction toward the second body access.

10. The pharmaceutical waste disposal assembly of claim 9 wherein the first waste receiver is a solid waste receiver including a solid receiver body that receives the solid pharmaceutical waste, and wherein the second waste receiver is a fluid waste receiver including a fluid receiver body that receives the fluid pharmaceutical waste.

11. The pharmaceutical waste disposal assembly of claim 9 wherein the second waste receiver is removable from the receiver retainer.

12. The pharmaceutical waste disposal assembly of claim 1 wherein the first waste guide includes a guide flap near the first body access, the guide flap moving between an open position and a closed position such that when the first waste receiver is moved to an inverted position, the guide flap moves to the closed position so that the pharmaceutical waste is inhibited from exiting the first receiver body.

13. The pharmaceutical waste assembly of claim 1 wherein the first waste guide inhibits removal of the pharmaceutical waste from the first receiver body.

14. A method for disposing of one or more of fluid pharmaceutical waste and solid pharmaceutical waste, the method comprising the steps of:
   receiving the pharmaceutical waste with a first receiver body of a first waste receiver directly through a first body access;
   substantially enclosing the first waste receiver within a receiver retainer;
   guiding the pharmaceutical waste in a first direction away from the first body access with a first waste guide; and
   guiding the pharmaceutical waste in a second direction toward the first body access with the first waste guide.

15. The method of claim 14 wherein the step of guiding the pharmaceutical waste in the first direction includes one of the first waste receiver and the receiver retainer including the first waste guide.

16. The method of claim 14 wherein the step of directly receiving includes the step of directly receiving the solid pharmaceutical waste with a solid receiver body of a solid waste receiver.

17. The method of claim 14 wherein the step of directly receiving includes the step of directly receiving the fluid pharmaceutical waste with a fluid receiver body of a fluid waste receiver.

18. The method of claim 14 wherein the step of guiding the pharmaceutical waste in the first direction includes the step of guiding the pharmaceutical waste in the first direction away from the first body access with the first waste guide prior to guiding the pharmaceutical waste in the second direction toward the first body access with the first waste guide.

19. The method of claim 14 further comprising the step of guiding the pharmaceutical waste in a third direction away from the first body access with the first waste guide prior to guiding the pharmaceutical waste in the second direction toward the first body access with the first waste guide.

20. The method of claim 14 further comprising the steps of guiding the pharmaceutical waste in a third direction away from the first body access with a second waste guide, and guiding the pharmaceutical waste in a fourth direction toward the first body access with the second waste guide.

21. The method of claim 14 further comprising the steps of directly receiving the pharmaceutical waste with a second receiver body of a second waste receiver through a second body access; substantially enclosing the second waste receiver within the receiver retainer; guiding the pharmaceutical waste in a third direction away from the second body access with a second waste guide; and guiding the pharmaceutical waste in a fourth direction toward the second body access with the second waste guide.

22. The method of claim 21 wherein the step of directly receiving the pharmaceutical waste with the first receiver body includes the step of directly receiving the solid pharmaceutical waste with a solid receiver body, and wherein the step of directly receiving the pharmaceutical waste with the second receiver body includes the step of directly receiving the fluid pharmaceutical waste with a fluid receiver body.

23. The method of claim 14 further comprising the steps of positioning a guide flap near the first body access, and inhibiting the pharmaceutical waste from exiting the first receiver body with the guide flap when the first receiver body is moved to an inverted position.

24. The method of claim 14 further comprising the step of inhibiting removal of the pharmaceutical waste from the first receiver body with the first waste guide.

25. A pharmaceutical waste disposal assembly for disposing of fluid pharmaceutical waste and solid pharmaceutical waste, the pharmaceutical waste disposal assembly comprising:
 a solid waste receiver including a solid receiver body having a solid body access, the solid pharmaceutical waste moving in a first direction toward the solid body access through which the solid pharmaceutical waste is received by the solid receiver body;
 a fluid waste receiver including a fluid receiver body having a fluid body access, the fluid pharmaceutical waste moving in a second direction toward the fluid body access through which the fluid pharmaceutical waste is directly received by the fluid receiver body; and
 a receiver retainer that substantially encloses the solid waste receiver and the fluid waste receiver, the solid waste receiver and the fluid waste receiver being removable from the receiver retainer;
 wherein one of the solid waste receiver and the receiver retainer includes a solid waste guide that guides the solid pharmaceutical waste in a third direction away from the solid body access and in the first direction toward the solid body access; and
 wherein one of the fluid waste receiver and the receiver retainer includes a fluid waste guide that guides the fluid pharmaceutical waste in a fourth direction away from the fluid body access and in the second direction toward the fluid body access.

\* \* \* \* \*